(12) United States Patent
Weber et al.

(10) Patent No.: US 7,899,221 B2
(45) Date of Patent: Mar. 1, 2011

(54) DEVICES AND METHODS FOR PRODUCING DENTURE PARTS

(75) Inventors: Gerhard Weber, Inning (DE); Stephan Holzner, Muehldorf am Inn (DE)

(73) Assignee: Institut Straumann AG, Basel (CH)

( * ) Notice: Subject to any disclaimer, the term of this patent is extended or adjusted under 35 U.S.C. 154(b) by 1710 days.

(21) Appl. No.: 11/095,027

(22) Filed: Mar. 31, 2005

(65) Prior Publication Data

US 2005/0214716 A1    Sep. 29, 2005

Related U.S. Application Data

(63) Continuation of application No. PCT/DE03/03462, filed on Oct. 20, 2003.

(30) Foreign Application Priority Data

Oct. 18, 2002 (DE) ................. 202 16 119

(51) Int. Cl.
   *G06K 9/00* (2006.01)
   *G06F 19/00* (2006.01)
   *A61C 13/00* (2006.01)

(52) U.S. Cl. ............... 382/128; 382/154; 700/95; 700/117; 433/191; 433/199.1; 433/213

(58) Field of Classification Search ......... 382/128–132, 382/154; 700/95–98, 117–118; 433/191–193, 433/199.1–203.1, 213–214
See application file for complete search history.

(56) References Cited

U.S. PATENT DOCUMENTS 3,861,044 A    1/1975    Swinson, Jr.

(Continued)

FOREIGN PATENT DOCUMENTS

DE    44 39 307 A1    5/1996

(Continued)

OTHER PUBLICATIONS

International Search Report for PCT/DE2001/04177 filed Nov. 8, 2001.

(Continued)

*Primary Examiner*—Manav Seth
(74) *Attorney, Agent, or Firm*—Martin Fleit; Paul D. Bianco; Fleit Gibbons Gutman Bongini & Bianco PL

(57) ABSTRACT

Surface mapping and/or generation device is provided, with a device for mapping 3D data of at least one denture base object such as a tooth stump or an implantation abutment, and an environment thereof, as well as with a device for the data-based generation and production of a denture part incorporating the 3D data of the denture base object. Additionally provided are a device for determining and/or defining a placement direction of the denture part that is to be slipped onto the denture base object, and a device for determining and producing a primary part that is to be slipped onto the denture base object before the denture part and that yields a desired placement direction for the denture part which is different from the placement direction that exists for slipping the primary part onto the denture base object. The device for data-based generation and production of a denture part is designed to generate and produce the latter by incorporating the 3D data of the primary part. Surface mapping and/or generation method is provided, wherein 3D data from a denture base object such as a tooth stump or an implantation abutment and an environment thereof are mapped and then, based on this 3D data of the denture base object, a denture part to be slipped thereon is produced. Before production of the denture part, a placement direction of the denture part onto the denture base object is determined or defined. On the basis of this 3D data of the denture base object, a primary part is determined and produced, with which a desired placement direction that differs from the placement direction that exists for slipping the primary part onto the denture base object is created for the denture part. On the basis of the 3D data, the denture part is generated and produced based on data so as to fit when pushed onto the primary part.

20 Claims, 20 Drawing Sheets

U.S. PATENT DOCUMENTS

| | | | |
|---|---|---|---|
| 4,478,580 A | 10/1984 | Barrut | |
| 4,575,805 A * | 3/1986 | Moermann et al. | 700/163 |
| 4,742,464 A | 5/1988 | Duret | |
| 4,964,770 A | 10/1990 | Steinbichler et al. | |
| 5,092,022 A | 3/1992 | Duret | |
| 5,184,306 A | 2/1993 | Erdman et al. | |
| 5,237,998 A * | 8/1993 | Duret et al. | 600/476 |
| 5,347,454 A | 9/1994 | Mushabac | |
| 5,401,170 A | 3/1995 | Nonomura | |
| 5,690,490 A | 11/1997 | Cannon et al. | |
| 5,718,585 A * | 2/1998 | Dehoff et al. | 433/202.1 |
| 5,816,810 A | 10/1998 | Antonson et al. | |
| 5,857,853 A | 1/1999 | van Nifterick et al. | |
| 5,873,721 A | 2/1999 | Willoughby | |
| 5,989,029 A | 11/1999 | Osorio et al. | |
| 6,049,743 A | 4/2000 | Baba | |
| 6,062,861 A | 5/2000 | Andersson | |
| 6,099,314 A * | 8/2000 | Kopelman et al. | 433/213 |
| 6,231,339 B1 | 5/2001 | Sharky | |
| 6,287,121 B1 | 9/2001 | Guiot et al. | |
| 6,364,660 B1 | 4/2002 | Durbin et al. | |
| 6,463,344 B1 * | 10/2002 | Pavloskaia et al. | 700/98 |
| 6,532,299 B1 * | 3/2003 | Sachdeva et al. | 382/128 |
| 6,694,212 B1 | 2/2004 | Kennedy | |
| 6,697,164 B1 | 2/2004 | Babayoff | |
| 6,788,986 B1 | 9/2004 | Traber et al. | |
| 6,848,909 B1 | 2/2005 | Persson | |
| 6,851,949 B1 * | 2/2005 | Sachdeva et al. | 433/213 |
| 6,970,760 B2 * | 11/2005 | Wolf et al. | 700/163 |
| 7,006,952 B1 * | 2/2006 | Matsumoto et al. | 703/2 |
| 7,020,325 B2 * | 3/2006 | Park | 382/154 |
| 7,027,642 B2 * | 4/2006 | Rubbert et al. | 382/154 |
| 7,058,213 B2 * | 6/2006 | Rubbert et al. | 382/128 |
| 7,065,243 B2 * | 6/2006 | Boland et al. | 382/154 |
| 7,068,825 B2 * | 6/2006 | Rubbert et al. | 382/128 |
| 7,110,594 B2 * | 9/2006 | Jones et al. | 382/154 |
| 7,123,767 B2 * | 10/2006 | Jones et al. | 382/154 |
| 7,197,179 B2 * | 3/2007 | Rubbert et al. | 382/154 |
| 7,305,110 B2 * | 12/2007 | Rubbert et al. | 382/128 |
| 7,342,668 B2 * | 3/2008 | Quadling et al. | 356/603 |
| 7,373,286 B2 * | 5/2008 | Nikolskiy et al. | 703/7 |
| 7,379,584 B2 * | 5/2008 | Rubbert et al. | 382/154 |
| 7,399,181 B2 | 7/2008 | Weber et al. | |
| 7,596,287 B2 * | 9/2009 | Wolf et al. | 382/312 |
| 7,609,875 B2 * | 10/2009 | Liu et al. | 382/154 |
| 7,689,310 B2 * | 3/2010 | Kopelman et al. | 700/98 |
| 7,698,014 B2 * | 4/2010 | Dunne et al. | 700/118 |
| 7,711,447 B2 * | 5/2010 | Lu et al. | 700/187 |
| 7,724,932 B2 * | 5/2010 | Ernst et al. | 382/128 |
| 2002/0028418 A1 * | 3/2002 | Farag et al. | 433/29 |
| 2002/0036617 A1 | 3/2002 | Pryor | |
| 2002/0044682 A1 | 4/2002 | Weil | |
| 2002/0055800 A1 * | 5/2002 | Nikolskiy et al. | 700/98 |
| 2002/0081554 A1 | 6/2002 | Marshall | |
| 2002/0137001 A1 | 9/2002 | Whiteman et al. | |
| 2002/0137011 A1 | 9/2002 | Shoher et al. | |
| 2003/0012423 A1 * | 1/2003 | Boland et al. | 382/154 |
| 2003/0031977 A1 | 2/2003 | Bodenmiller et al. | |
| 2003/0096214 A1 | 5/2003 | Luthardt | |
| 2004/0032594 A1 | 2/2004 | Weber | |
| 2004/0158342 A1 | 8/2004 | Wolf et al. | |
| 2005/0214716 A1 | 9/2005 | Weber et al. | |
| 2006/0063135 A1 | 3/2006 | Mehl | |
| 2006/0099549 A1 | 5/2006 | Engman | |
| 2006/0106484 A1 | 5/2006 | Saligner et al. | |
| 2007/0128580 A1 | 6/2007 | Mormann | |
| 2008/0050700 A1 | 2/2008 | Weber et al. | |
| 2008/0131833 A1 | 6/2008 | Weber | |
| 2008/0153069 A1 | 6/2008 | Holzner et al. | |
| 2008/0154743 A1 | 6/2008 | Holzner et al. | |

FOREIGN PATENT DOCUMENTS

| | | |
|---|---|---|
| DE | A 44 39 307 | 5/1996 |
| DE | 196 05 741 | 7/1997 |
| DE | 19642247 | 1/1998 |
| DE | 44 39 307 | 5/1998 |
| DE | 19710273 | 8/1998 |
| DE | 197 21 688 | 9/1998 |
| DE | A 197 21 688 | 9/1998 |
| DE | 19930564 | 10/2000 |
| DE | 102 14 968 | 10/2003 |
| EP | 0 054 785 | 6/1982 |
| EP | 0054785 A1 | 6/1982 |
| EP | 0490848 | 6/1992 |
| EP | 0643948 | 3/1995 |
| EP | 0 913 130 | 5/1999 |
| EP | 0913130 A2 | 5/1999 |
| EP | 0913130 A2 | 5/1999 |
| EP | 1 062 916 A2 | 12/2000 |
| EP | 1062916 | 12/2000 |
| EP | 1088620 | 4/2001 |
| EP | 1208811 | 5/2002 |
| EP | 1293174 | 3/2003 |
| EP | 1 506 745 A1 | 2/2005 |
| EP | 1 558 893 | 8/2005 |
| ES | 2193450 | 5/1999 |
| JP | 2000-185060 A | 7/2000 |
| JP | 2001-54525 A | 2/2001 |
| JP | 2001-518815 T | 10/2001 |
| WO | WO 94/27523 | 12/1994 |
| WO | WO 97/35439 | 9/1997 |
| WO | 98/44865 A1 | 10/1998 |
| WO | 01/32092 A1 | 5/2001 |
| WO | WO 02/09612 | 2/2002 |
| WO | 02/39056 A1 | 5/2002 |
| WO | WO 02/39056 | 5/2002 |
| WO | WO 02/076327 | 10/2002 |
| WO | WO 03/007834 | 1/2003 |
| WO | WO 03/017864 | 3/2003 |
| WO | WO 03/024352 | 3/2003 |
| WO | WO 03/057067 | 7/2003 |
| WO | 03/105710 | 12/2003 |
| WO | WO 2004/030565 | 4/2004 |
| WO | 2004/038326 | 5/2004 |
| WO | WO 2004/037112 | 5/2004 |
| WO | WO 2004/038326 | 5/2004 |
| WO | WO 2004/044787 A | 5/2004 |
| WO | WO 2004/060197 | 7/2004 |
| WO | WO 2006/005284 | 1/2006 |

OTHER PUBLICATIONS

International Preliminary Examination Report PCT/DE2001/04177 filed Nov. 8, 2001.

European Search Report for EP 07001160.6 (European case related to U.S. Appl. No. 12/026,617).

European Search Report for EP 07001054.1 (European case related to U.S. Appl. No. 12/026,617).

European Search Report for EP 07001056.6 (European case related to U.S. Appl. No. 12/026,617).

International Preliminary Report on Patentability for PCT/DE2003/003462 filed Oct. 20, 2003.

International Search Report for PCT/DE2003/003462 filed Oct. 20, 2003.

European Search Report for 01 993 809.1 (European case related to U.S. Appl. No. 12/026,617).

English Translation of International Preliminary Examination Report published Apr. 18, 2005 for PCT/DE03/03462 filed Oct. 20, 2003.

Fairpo, Jenifer E. H. et al.: Heinemann Dental Dictionary Fourth Edition; Reed Educational Professional Publishing Ltd. 1997.

Kucey, Brian K.S et al.: The Procera Abutment—The Fifth Generation Abutment for Dental Implants; Journal of the Canadian Dental Association 2000; 66: pp. 445-449; Sep. 2000, vol. 66, No. 8.

Lima Verde, Marcus A.R. et al.: Technique To Restore Unfavorably Inclined Implants; The Journal of Prosthetic Dentistry 1994;71: pp. 359-363 (Apr. 1994).

Felber, Leo et al.: Computergestutzte Vollautomatischekonstruktion Von Inlays; Acta Med Dent Helv, vol. 2:Sep. 1997, pp. 217-225.

Dental Dialogue: Das Internationale Journal fur die Zahntechnik; Mit freundlicher Empfehlung.

Notice of Opposition filed by 3M Innovative Properties Company for EP Appl. 03776796.9 (related application).

Annex I to Opposition filed by 3M Innovative Properties Company for EP Appl. 03776796.9 (related application).

Gerhard Geiger, Geschiepe Technik, 1982.

* cited by examiner

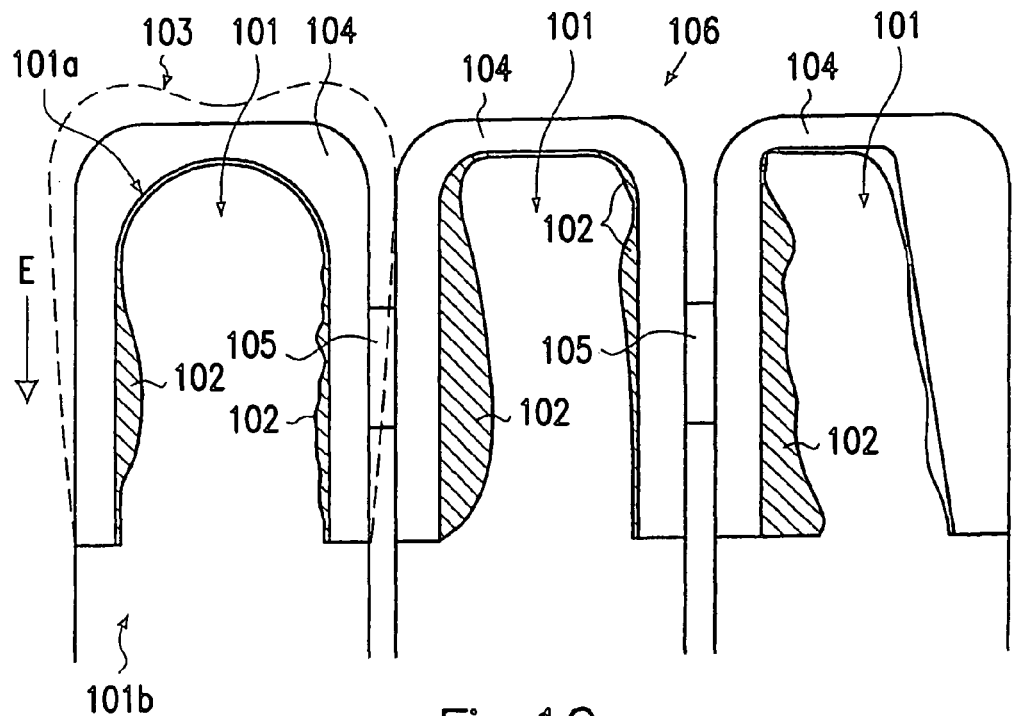
Fig. 10
PRIOR ART
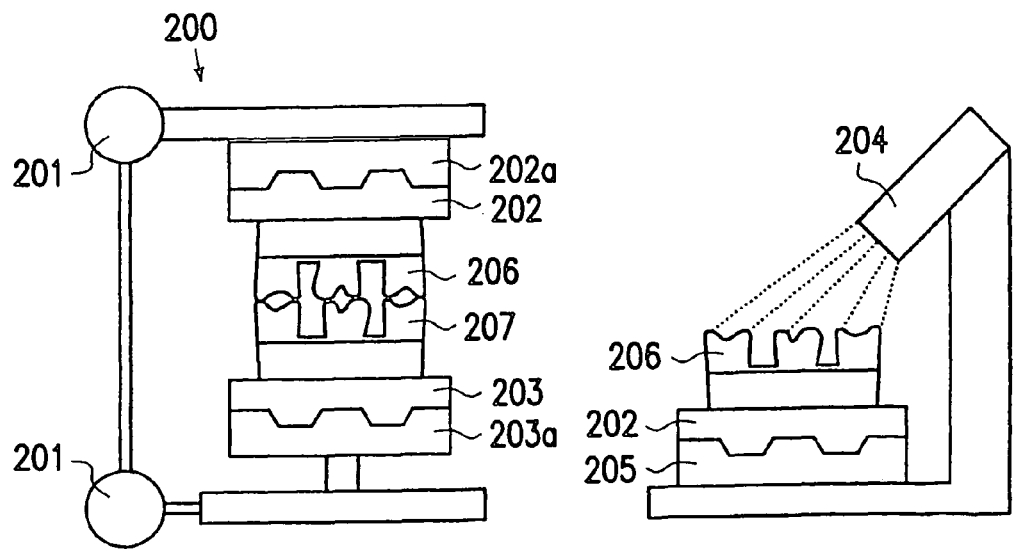
Fig. 11
PRIOR ART
Fig. 12
PRIOR ART

DEVICES AND METHODS FOR PRODUCING DENTURE PARTS

RELATED APPLICATION

This application is a continuation of International Patent Application Serial No. PCT/DE 2003/003462, filed Oct. 20, 2003, the contents of which are here incorporated by reference in their entirety.

BACKGROUND OF THE INVENTION

1. Field of the Invention

The present invention pertains to devices and methods for producing denture parts, more particularly, using surface mapping and generation devices as well as to methods for surface mapping and surface generation for mapping and/or generating surfaces of teeth.

2. Prior Art

Fundamental technologies that can be used together with the present invention, or with which it can be combined, are disclosed in laid-open patents DE 44 39 307 A1 and DE 197 21 688 A1 as well as WO 02/39056 A1, which can be cited, on the one hand, as the closest prior art for surface mapping and generation and methods for surface mapping and generation and, on the other hand, are herewith incorporated in full by reference into the present documents, since the present invention can be used and combined in all its configurations with this technology and, in that sense, advantageously refines and/or improves it, wherein also lie objectives of the present invention in some of its aspects.

WO 02/39056 A1 discloses a large amount of useful and/or essential information that is useful or at least advantageous for the comprehension and design of the present invention, so that WO 02/39056 A1 is extensively cited below.

In the original version of WO 02/39056 A1, its technical teaching achieves the objective of creating a surface mapping and generation device with devices for optimizing the process and/or cost.

According to WO 02/39056 A1, it is preferably provided that the devices for optimizing the process and/or cost contain raw material recovery devices, and/or that the devices for optimizing the process and/or cost contain an automatic controlling of the intensity of a laser light that is employed. Alternatively or additionally, it is preferable for the devices for optimizing the process and/or cost to be laid out such that two half-frames that show different positions or views are evaluated, with a pulsed laser being contained in particular for exposure.

Further alternative or additional configurations of a surface mapping device according to WO 02/39056 A1, more particularly for obtaining surface data of teeth, consist in the fact that the devices for optimizing the process and/or cost contain devices for carrying out a calibration procedure by evaluating superimposition errors at matching points, and/or that an image-recording device, more particularly, a CCD chip is arranged such that lines lie perpendicular to the displacement direction of the measuring table, taking into account the Scheimpflug angle.

An additional variant of a surface mapping device especially for obtaining surface data of teeth according to WO 02/39056 A1 is that the devices for optimizing the process and/or cost contain, in particular, devices for archiving three-dimensional jaw data and/or for simulating the bite position of the upper and lower jaws.

Special, preferably mechanical configurations of the surface mapping device are oriented according to the disclosures of FIGS. 3 and 4 and/or 5, 6 and 7 as well as the related description.

It is additionally preferred if, in the surface mapping and generation device especially for producing dentures, the devices for optimizing the process and/or cost contain devices for the optimized preparation of at least one tooth stump for the production and for the placement of a dental prosthesis thereon and/or devices for taking into account the bite position of the upper and lower jaws.

The surface mapping and/or generation methods according to WO 02/39056 A1 are characterized in that they contain one or more of the above-explained devices or function analogously thereto.

Finally, a patient data archival system that is characterized by a chip card and/or decentralized data storage units especially for tooth data is created by WO 02/39056 A1.

Individual aspects of WO 02/39056 A1 will be explained in even more detail below.

According to one aspect of WO 02/39056 A1, starting from surface mapping technologies, devices and methods as specified in the above-indicated publications, herein incorporated by reference, and subsequently referred to for simplicity as "scanners" or "scanning," a raw material recovery means is provided in combination with, for instance, a milling machine. Together with the milling machine and an appropriate data processing system, the scanner constitutes a CAD-CAM system specifically for the production of gold or platinum dentures. The raw material recovery can preferably be implemented by equipping the milling machine, for instance, with, as one example, means for the suction of gold or platinum dust/chips. Considering the high costs for the raw materials gold or platinum, a considerable reduction of the costs for producing gold or platinum dentures is thereby advantageously achieved.

According to another aspect of WO 02/39056 A1, the scanner technology disclosed in the above-mentioned publications is further improved.

First, this is achieved according to WO 02/39056 A1 by an automatic regulation of the intensity of the laser light that is employed. Therein, the reflectivity of the [word omitted] to be mapped is detected via, for instance, the intensity of the light received by a CCD chip. The intensity of the laser light is then re-regulated based on the detection result. The improvement in this configuration is that measurement errors due to undershooting or overshooting of the measurement signal are thereby reduced. WO 02/39056 A1 pertains both to devices and to methods in keeping with the above explanation.

Second, the scanner technology within the scope of WO 02/39056 A1 is improved by an increase in speed in that, instead of a full frame from the camera/CCD chip consisting of two combined half-frames, two such half-frames that show different views are analyzed. The different views result from different relative positions of the tooth surface to be mapped and the device for recording this surface (e.g., a lone CCD chip or a camera therewith).

Particularly the above improvement, and also the scanning technology in general, can be advantageously refined by driving the laser being used in a pulsed mode similar to a stroboscopic effect and, for example, by displacing the table bearing the object whose surface is to be mapped, such as a tooth or a model thereof, particularly if this is done continuously. By virtue of the pulsed laser beam, instantaneous images or "still images" are prepared for each relative position of object and camera, since the object appears to be stationary during the brief time of exposure with one laser pulse and can be recorded by the camera in this position. It is particularly preferable for each individual laser pulse to be coupled to the recording of one half-frame.

Yet an additional improvement of scanner technology according to WO 02/39056 A1 lies in a calibration procedure, which corrects various spatial distortions of the ascertained measurement parameters. A body is measured in this case from several different views. The measurements are put together by way of matching algorithms. The superimposition errors occurring at various points of the object in this process are analyzed with regard to recognizing deviations in all directions. These deviations yield calibration errors, from which in turn calibration parameters in all directions and rotations of space are calculated. These calibration parameters can then automatically be taken into account by the data-processing system in additional measurements, whereby an enhanced measurement precision is advantageously achieved. Additional details in this regard can be deduced from the embodiment illustrated in FIG. 1.

Moreover, the scanner according to the even older prior art is improved by WO 02/39056 A1 in that a CCD chip (or in general a surface image mapping device) is arranged such that, for example, taking into account the Scheimpflug angle, the camera lines are perpendicular to, for example, the displacement direction of the measuring table on which the object to be mapped is installed. Additional details in this regard are illustrated in the embodiment according to FIG. 2. Thereby, a better utilization of the measuring field for surveying, teeth for example, is achieved; it must be noted that ordinary commercial chips are not square.

The known scanner technology can also be improved further by positioning and arranging the displacement and pivot axes of the object carrier, the object and/or the camera according to WO 02/39056 A1 such that a view into all the undercuts occurring in the jaw is possible if the teaching of WO 02/39056 A1 is utilized in, for instance, the field of dental surface mapping. This has the advantage that a completely automatic surveying/measuring strategy can be utilized.

According to another aspect of WO 02/29056 A1, diverse data-processing modules are advantageously used in different fields of dentistry.

Thus, WO 02/39056 A1 creates a scanner technology that is equipped with a data-processing system, preferably in the form of a standard computer with special software as the control unit, that is suitable for archiving, for instance, three-dimensional jaw data, more particularly, surface data. The archiving serves to replace previous archiving of such data in the form of plaster casts. In many fields of dentistry, it was previously necessary to preserve plaster casts of patients for up to 10 years, which resulted in an enormous demand for space. The electronic archiving of these data not only provides a remedy with regard to space needs; it also enables a faster, simpler and more economical utilization of the archived data. This it is possible, for instance, to acquire and archive 3D measurement data from previously healthy tooth surfaces. If, for instance, a tooth is to be replaced years later, this allows a reconstruction of the tooth in the form of a denture that can be produced, for example, on the basis of the archived data by generating its surfaces with milling technology.

Electronic archiving of jaw/bite data can also be advantageously used in many other respects, however. Thus, these data enable, by means of a suitable data-processing system, a simulation of the bite position of the upper and lower jaw. More particularly, this can be generated by first surveying the lower jaw, then placing a bite record (impression in the patient's mouth while biting) on top of the lower jaw and surveying it again. Thus both surfaces are acquired in the biting situation. The two data records can be displayed separately or together and all the associated dental analyses can be carried out, e.g., qualitatively or quantitatively (in the form of distance or volume measurements). As a complement, the complete upper jaw can be surveyed and spatially referenced by means of the bite record and, for instance, a matching software. Mastication motions can likewise be simulated on the computer by recording the jaw movement and the bite record. The referencing of the measurement data from the upper and lower jaws can also be employed for the modulation of a denture in connection with CAD-CAM technology.

An additional variant of WO 02/39056 A1 consists in a scanner technology with a data-processing system in the form, for instance, of a standard computer with suitable software as the control unit, so as also to be able to simulate the bite position of the upper and lower jaws with a particular orientation for an orthopedic treatment of the jaw. A treatment plan for a brace, for instance, can be simulated by subdividing in the software the dentition in tooth groups all the way down to individual teeth, to cite one possible example. Such groups of teeth or individual teeth can be moved and the final positions simulated. This permits answers to questions of whether the required space is available on the jaw ridge and what the bite will look like after therapy. Monitoring of therapy is possible with additional data-processing/software units, which can be combined modularly. A jaw can be repeatedly scanned at time intervals. The temporally successive images can then be played back as an interpolated "film." This allows a comparison of the course of the actual treatment with the planned treatment and the formulation/performance of corrective measures. Such image series can, moreover, be archived and can make it easier, for instance, to provide evidence in lawsuits. Communication with expert committees and insurance companies is also facilitated.

Another aspect of WO 02/39056 A1 is a scanner technology that is equipped with a data-processing/electronic controller (by software, for instance) in order, for example, to simulate the bite position of the upper and lower jaws with particular orientation for oral-surgical therapy. Within the scope of this aspect of WO 02/39056 A1, in particular, the incorporation of measurement data of the jawbone (acquired, e.g., by computer tomography) is provided, by means of suitable software. The planning of therapy (an operation on the jaw, for example) is simulated by subdividing the dentition, the jaw and the jawbone into tooth/jaw section groups (all the way down to individual teeth) in, for example, software. The tooth groups/individual teeth can be moved and the final positions simulated. This enables the answering of questions as to whether the required space is available and what the patient will look like after the therapy. An additional data-processing/software module can be utilized in this case for monitoring the therapy. After segments of time have elapsed, the current status each time can be scanned. The images over time can then be played back as an interpolated "film." The course of the actual treatment can be compared with the planned treatment and any necessary corrective measures can be derived therefrom. In an advantageous manner, this aspect of WO 02/39056 A1 enables the planning and simulation of implants. Archived image series to facilitate the provision of evidence in possible lawsuits and simpler, faster communication with expert committees and insurance companies are additional advantages.

Finally, a patient-data carrier such as a chip card that contains all person-related health and illness data also lies within the scope of WO 02/39056 A1. Such an individual data carrier can be integrated into a management and archiving system that, in particular, contains decentralized storage units for archiving large amounts of data which can be accessed by means of access devices on the data carrier. Thus, for instance, even master dental patient data, which can contain 3D jaw and individual tooth data of tooth surfaces and internal structures of individual teeth as well as generation data of dentures in use (material and milling data for example), can be archived and made easily available. Additionally, health insurance data, digital X-ray images, previous and current attending physicians and generally the entire medical history of a patient are stored. Special reading and analysis devices can also be provided within the technical teaching of WO 02/39056 A1 and, in certain circumstances, be integrated into the system. Advantages achieved here are, for instance, double archiving for the patient, better trace-back possibilities for health insurance agencies and data availability even in case of change of address.

The object of WO 02/39056 A1 is also an additional variant/configuration for the implementation of a pulsed measurement, as already presented in principle above.

A corresponding surface mapping unit or device consists, for example, of a linear table, a CCD camera, a frame grabber card and a laser line module. To acquire data, the laser line is permanently projected onto the object being measured. The measuring table is moved step-by-step underneath the measurement arrangement (laser line and CCD chip). After each step, there is a measurement.

The exact previous process in this regard is as follows. The measuring table moves into a start position and stops. The object must be stationary so that no "wobbling" of the image causes measuring inaccuracies. Then the CCD camera reads out a line (full-frame) and transfers the signal to the frame grabber card. Subsequently, the table is accelerated (starting ramp). Then the table is again braked and stopped in a specified position (braking ramp). The CCD camera then reads out the next line. This entire process runs in a darkened room. The laser diode can be regulated up only to a certain power if the signal is not to overshoot.

According to WO 02/39056 A1, it was an innovation at that time for the laser line to be projected stroboscopically onto the measured object, that is for light flashes to be regularly cast in the form of a laser line onto the object. The measuring table moves the object continuously beneath the measuring arrangement (laser line, CCD chip). A measurement takes place simultaneously with each light flash. In particular, the measuring table travels at a controlled/monitored speed that is matched to the flash controller. A flash is emitted at preferably regular intervals (time or travel distance of the table) and simultaneously a half-frame is read out from the CCD chip. This signal is transferred to the frame grabber card and analyzed by means of special software. The flash time is sufficiently short that "wobbling" that could result from the continuous table movement is negligible.

With the configuration from WO 02/39056 A1, the measuring process is accelerated by a factor of 5, since the startup and braking times of the table are eliminated and the light flashes are clocked sufficiently fast that half-frames can be read out. Another advantage resulting is that the controller can be designed more economically, since only a uniform feed rate need be guaranteed and it is not necessary to set a precise resting position. It is also advantageous that earlier optomechanical arrangements can continue to be used/employed, since the present innovation can be implemented or already exists in regard to controlling, regulation and software for the components. It is additionally advantageous that the flash used is considerably more intense than the laser signal previously used, whereby the measurement can be taken even in daylight and the measuring room need not be darkened, which considerably reduces the work and its cost and time requirements, particularly when measurement objects are changed.

Alongside the technical specifications on the subject of "stroboscopic laser" already specified above and just preceding, the scope of WO 02/39056 A1 also includes mechanical embodiments which, in their concept and concrete configurations as well as their operating methods, are considered worthy of protection and protectable, in combination and also on their own.

Particularly in comparison to the technical status of the device for producing a denture according to EP 98115809.0, WO 02/39056 A1 contains a number of concepts and configurations that render a corresponding device drastically more economical to produce and more secure in operation. These aspects of WO 02/39056 A1 also constitute advantageous and preferred refinements and combinations of the technology disclosed in DE 44 39 307 A1 and DE 197 21 688 A1, the entire content of which, as well as that of the laid-open publication of EP 98115809.0 are herewith incorporated in full into the present documents in order to avoid mere identical repetition. The individual characteristics and combinations of characteristics can, in particular, be combined with the above-explained stroboscopic technology, although this is not mandatory or exclusive.

SUMMARY OF THE INVENTION

For instance, based on and/or in combination with the preceding explanations from PCT/DE01/04177 (International Publication No. WO 02/39056 A1), but not limited to such a basis or combination, the present invention has further improvements in devices and methods for the production of denture parts as its objective.

To achieve this objective, the present invention creates:
devices and methods for partially or fully automatic edge recognition of inlay preparations and
devices and methods for producing complex denture designs.

The advantages of these devices and methods according to the invention lie particularly in their process and time optimization.

In particular and primarily, but not restrictively, technical improvements over and against the technical teaching in EP 98115809.0 and WO 02/39056 A1 are created with the individual aspects of the present invention. It is again emphasized that the devices and methods according to the invention for producing denture parts can specifically be implemented even without the basis of and/or combination with the technology of the aforesaid prior art and are therefore worthy of protection.

Devices and methods for producing denture parts according to the invention are specified in the independent claims. Additional preferred and advantageous configurations of the invention can be deduced from the individual claims and combinations thereof.

More particularly, the present invention creates surface mapping and/or generation devices, with devices for mapping 3D data of at least one denture base object such as a tooth stump or implantation abutment and an environment thereof, as well as with devices for data-based generation and production of a denture part by incorporating the 3D data of the denture base object, wherein there are additionally provided: devices for detecting and/or defining a placement direction of the denture part that is to be pushed on the denture base object, as well as devices for detecting and producing a primary part that is to be pushed onto the denture base object before the denture part and yields a desired placement direction for the denture part which is different from the placement direction that is defined for pushing the primary part onto the denture base object, and such that the devices for data-based generation and production of a denture part are designed to generate and produce the latter by incorporating the 3D data of the primary part.

Preferred refinements are such that combination devices are additionally provided which are designed for assembling 3D data of at least 2 denture base objects with regard to their shape, position and attitude to one another and that the devices for producing a denture part are designed to produce a common denture part for all involved denture base objects.

It is additionally preferred if mapping devices operating contact-free are contained for mapping the shape, position and/or attitude of each denture base object and/or each primary part.

In yet another advantageous configuration of the present invention, it is provided that, for detecting and/or defining and/or generating and/or combining measurement data, 3D data and data records, archive and/or specification data and/or data records and placement directions, electronic processing devices are provided, to which processor devices, storage devices, interfaces and control devices are assigned, or in which processor devices, storage devices, interfaces and control devices are contained. Alternatively or additionally, it can preferably be provided that devices according to WO 02/39056 A1 are contained and/or that CAD-CAM devices are contained.

Within the scope of the present invention, it can additionally be provided that remote data transmission devices are contained, so that the mapping devices and in any case the generation devices and/or the production devices can be set up spatially separated from one another, with a plurality of spatially separated mapping devices preferably coupled to a central generation device.

Also created by the invention are surface mapping and/or generation methods, wherein 3D data of a denture base object, like a tooth stump or an implantation abutment, and an environment thereof are acquired and then, on the basis of these 3D data of the denture base object, a denture part to be pushed onto the latter is produced, with a placement direction of the denture part onto the denture base object being determined and/or defined before production of the denture part; on the basis of these 3D data of the denture base object, a primary part is determined and produced, with which a desired placement direction for the denture part is created that is different from the placement direction defined for pushing the primary part onto the denture base object; and the denture part fitted for being pushed onto the primary part is generated and produced on the basis of the latter's 3D data.

It can also preferably be provided here that 3D data from at least two denture base objects are acquired regarding their form, position and attitude with respect to one another, and that a common denture part for all the denture base objects involved is generated and produced based on data, with 3D data from at least two denture base objects preferably being acquired individually regarding their form, position and attitude with respect to one another and then assembled.

It can additionally be provided in the surface mapping and/or generation method according to the invention that the mapping of form, position and/or attitude of each denture base object and/or each primary part be done on a noncontact basis and/or that devices according to WO 02/39056 A1 be utilized.

In additional preferred configurations, it can be provided that measurement data, 3D data and data records, archive and/or specification data and/or data records as well as placement directions are employed, preferably from measuring devices and/or storage devices, with data from databases preferably being used for prefabricated parts.

It also lies within the preferred scope of the invention if CAD-CAM methods are contained and/or if the mapping of objects and particularly their 3D data and data records is done spatially separated from the production of primary parts and/or denture parts, making use of remote data transmission, preferably with mapping at a number of places being coupled by remote data transmission to central mapping [sic; generation] and/or production.

In combination with the foregoing configurations of surface mapping and/or generation devices, or also on its own, the invention also creates surface mapping and/or generation devices in which devices for partially or fully automatic edge detection of inlay preparations are provided and/or in which devices for the production of complex denture designs are provided.

Analogously, the foregoing surface mapping and/or generation methods according to the present invention, each on its own or in combination with the above indicated variants, contain surface mapping and/or generation methods with method steps for partially or fully automatic edge detection of inlay preparations and/or with method steps for the production of complex denture designs.

Beyond the above, the invention contains additional variants and aspects that are disclosed in the present description and in the appended drawings on the basis of special configurations or in the form of general statements. All of these variants and aspects are to be considered disclosed, each in its own right, as well as separately in any combination with other aspects and variants, and the basis for patenting is created by the present disclosure for each variant and each aspect on its own and in any combination of aspects and variants.

BRIEF DESCRIPTION OF THE DRAWINGS

The invention will be explained in greater detail below on the basis of embodiments, merely for the sake of example, with reference to the drawing, in which

FIG. 1b is a schematic front view of a jaw with drawn-in scanning strips as in FIG. 1a;

FIG. 10 is a schematic partial view of a jaw to explain an additional aspect of WO 02/39056 A1;

FIG. 11 is a schematic side view of a mastication or bite simulator to illustrate an additional aspect of WO 02/39056 A1;

FIG. 12 is a schematic side view of a jaw from FIG. 11 in a surface mapping device;

DETAILED DESCRIPTION OF PREFERRED EMBODIMENTS OF THE INVENTION

Figure 1A:
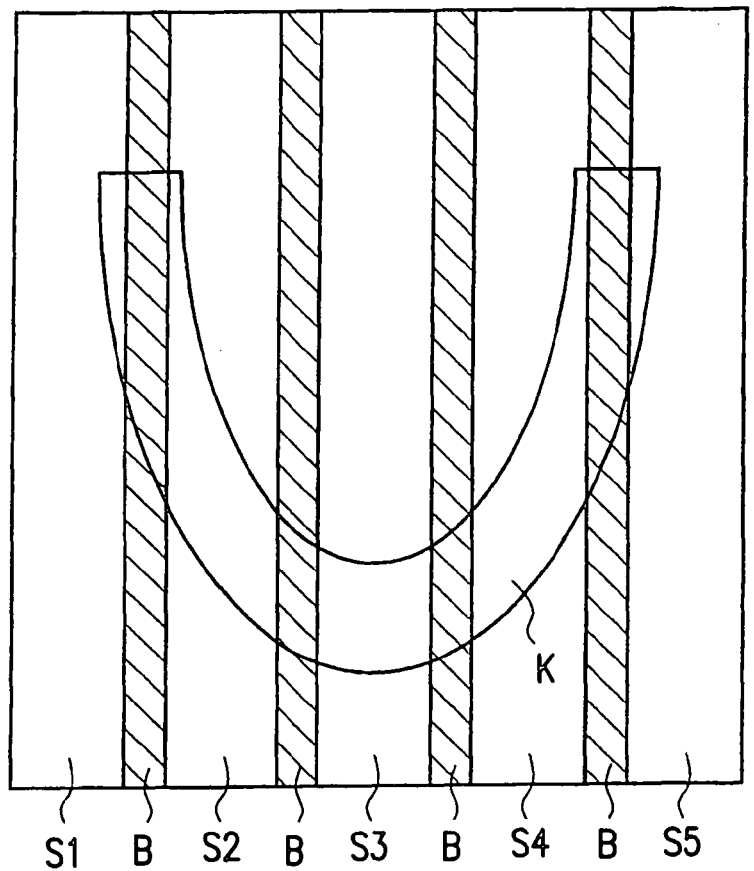
FIG. 1a is schematic plan view of a jaw with drawn-in scanning strips according to prior art.
Figure 1B:
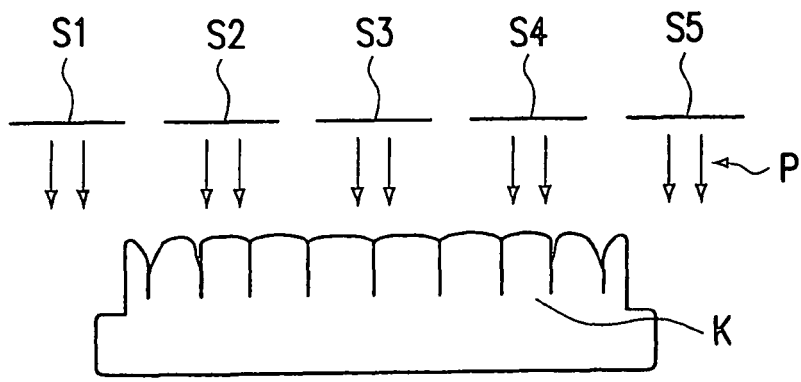

In the individual figures, identical or similar or identically or similarly acting parts are provided with the same reference numbers, or are shown comparably, so that parts as well as combinations thereof, their functions and their modes of action are immediately understandable to a person skilled in the art even from viewing the figures of the drawing alone, from comparing them and/or from the following statements, alone if desired, even if no references between specific figures and/or between figures and text are explicitly indicated or shown.

First, the technical teachings disclosed in WO 02/39056 A1 will be explained with reference to FIGS. 1-12, particularly in order to understand the function of a corresponding device and method as well as fundamentals of the production of dentures. This technology according to WO 02/39056 A1 can serve as a basis for the individual aspects of the present invention and be combined with the latter, which is not compulsory, however, for the implementation of the individual aspects of the present invention. The latter can be implemented and employed even without the technology according to WO 02/39056 A1, in conjunction with other technologies.

In FIGS. 1 and 2, a scanning of a jaw K is illustrated in a plan view and a front view. For example, five measuring strips S1, S2, S3, S4 and S5 are mapped one alongside the other. The five measuring strips S1-S5 overlap in areas B, which are shown cross-hatched in FIG. 1a and are omitted for comprehensibility in FIG. 1b. FIG. 1b serves only to illustrate the position of the measuring strips S1-S5 in a front view of the jaw K and the direction of the scanning radiation according to the arrows P. The overlap areas B enable the fitting together of the individual measuring strips by means of matching methods into an overall image of the jaw K.

Figure 1C:
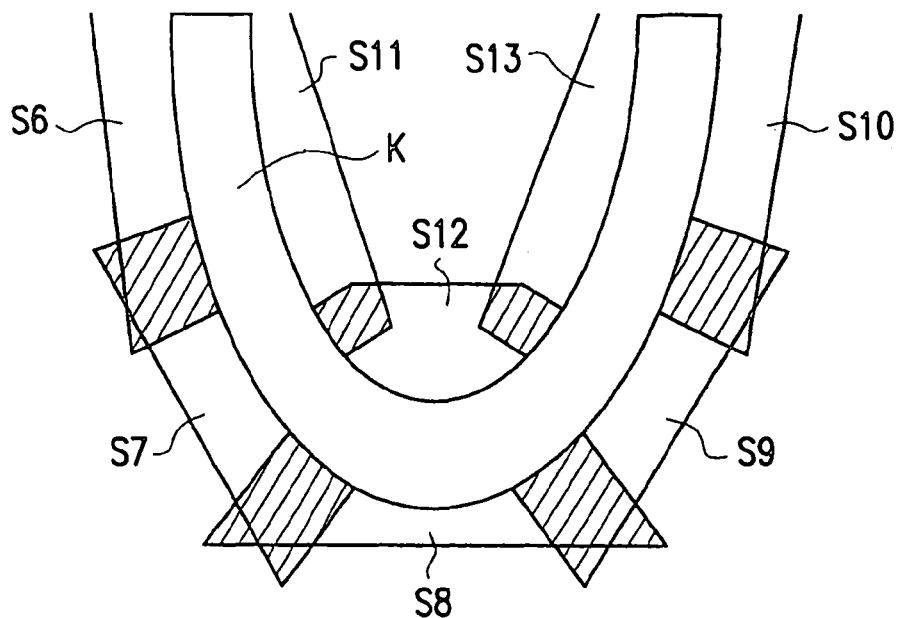
FIG. 1c is a schematic plan view of a jaw with drawn-in scanning strips according to WO 02/39056 A1.
Figure 1D:
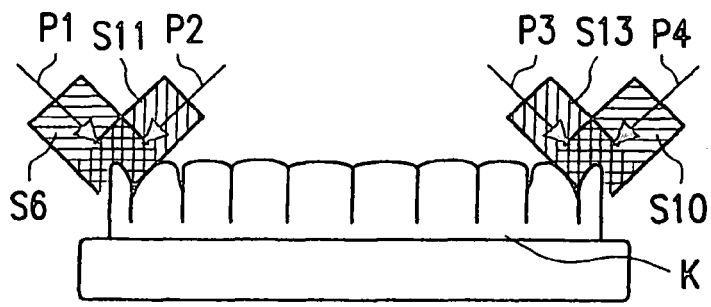
FIG. 1d is a schematic front view of a jaw with drawn-in scanning strips as in FIG. 1c.

A variant of the above technology according to WO 02/39056 A1 is likewise shown in FIGS. 1c and 1d in a plan view and a front view, respectively. In this methodology and with the appropriate devices, measuring strips S6, S7, S8, S9, S10, S11, S12 and S13 are generated, but consist only of so-called half-frames, so that more measuring strips are generated and processed than in FIGS. 1a and 1b, and these measuring strips get by with a considerably smaller volume of data. The position of the measuring strips S6-S13 with respect to the jaw K is shown in the plan view of FIG. 1c. The irradiation directions are shown schematically for the sake of example by arrows P1, P2, P3 and P4 for measuring strips S6, S11, S13 and S10 in FIG. 1d. In FIG. 1c, the overlap areas B of the individual adjacent measuring strips are again shown cross-hatched. By virtue of the irradiation directions that have been modified in relation to prior art, precise data of the jaw K are obtained, and with a smaller amount of data and processing than in prior art, by using only half-frames.

Figure 2A:
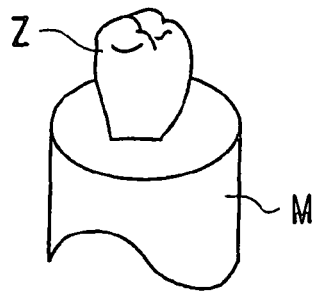
FIG. 2a is a schematic perspective view of a measurement object in the form of a tooth.

An individual measurement object in the form of a tooth Z is schematically shown in a perspective view in FIG. 2a, as installed in a measuring pot M that is filled in this case, for example, with a molding compound, into which the tooth Z is inserted at its lower end (not visible).

Figure 2B:
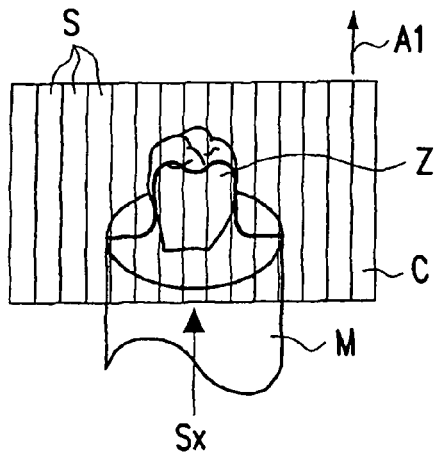
FIG. 2b is a schematic view of the measurement object from FIG. 2a with drawn-in scanning strips according to prior art.
Figure 2C:
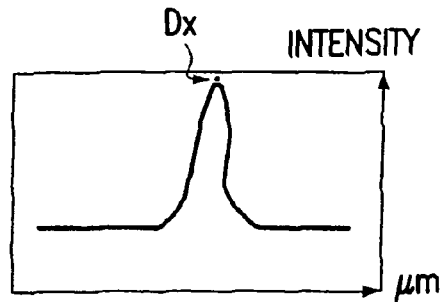
FIG. 2c is a schematic view of a signal graph of a scan line from FIG. 2b.

For this measurement object Z, the position of the measuring strips or measuring lines S is shown schematically in FIG. 2c [sic; 2b], and FIG. 2c shows the signal graph for a measuring strip or measuring line Sx in which only one measured point Dx is obtained. The reading direction (line direction) is also drawn into FIG. 2b with the arrow A1. A chip C as the measuring device, which can be a CCD chip or any other camera device, images the sum of all the measuring strips or measuring lines S.

Figure 2D:
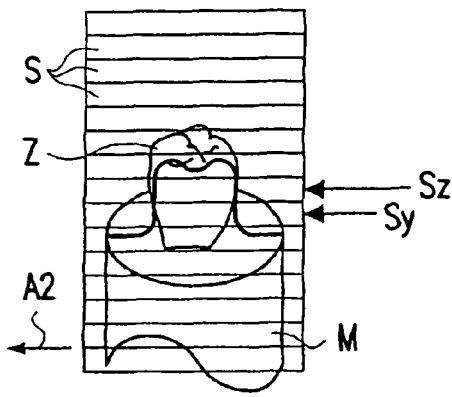
FIG. 2d is a schematic view of the measurement object from FIG. 2a with drawn-in scanning strips according to WO 02/39056 A1.
Figure 2E:
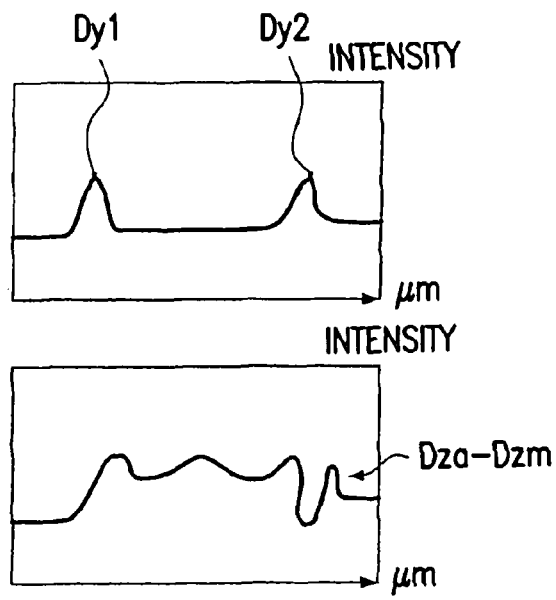
FIG. 2e is a schematic view of a signal graph of a scan line from FIG. 2d.

In a measuring line or measuring strip S according to WO 02/39056 A1, on the other hand, a plurality of measured points, e.g., Dy1 and Dy2 or Dza-Dzn, are obtained, as is illustrated by FIGS. 2d and 2e, which are representations analogous to FIGS. 2b and 2c. The readout direction in this case is according to arrow A2 in FIG. 2d, and the chip C as well as the position of the measuring strips or measuring lines S are consequently rotated by 90° in relation to prior art. Due to this arrangement, two measured points Dy1 and Dy2 are obtained in the measuring line Sy. The measurement in the line Sz even leads to a plurality of measured points Dza-Dzn. For the analysis, the chip arrangement is then interpolated and simulated by means of software, as in prior art (see FIG. 2b). The readout direction, obtained as in prior art, once again contains several measured points per line, which can be acquired computationally as point 1, then point 2, and so on. With this aspect of WO 02/39056 A1, more information is obtained with less effort by using only half-frames, so that the accuracy of WO 02/39056 A1 in relation to previous prior art increases.

Figure 3:
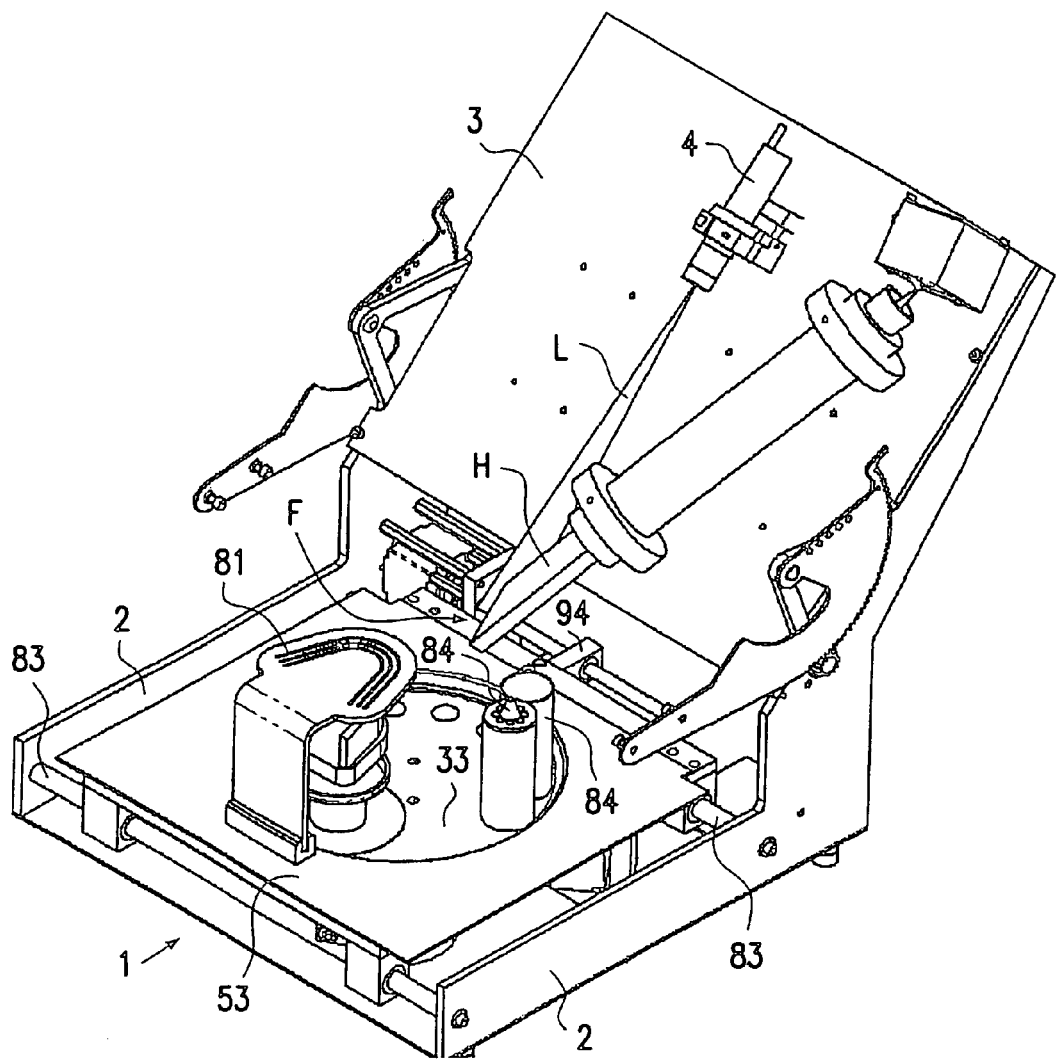
FIG. 3 is a schematic perspective view of one embodiment of a surface mapping device according to WO 02/39056 A1 from above at an angle.
Figure 4:
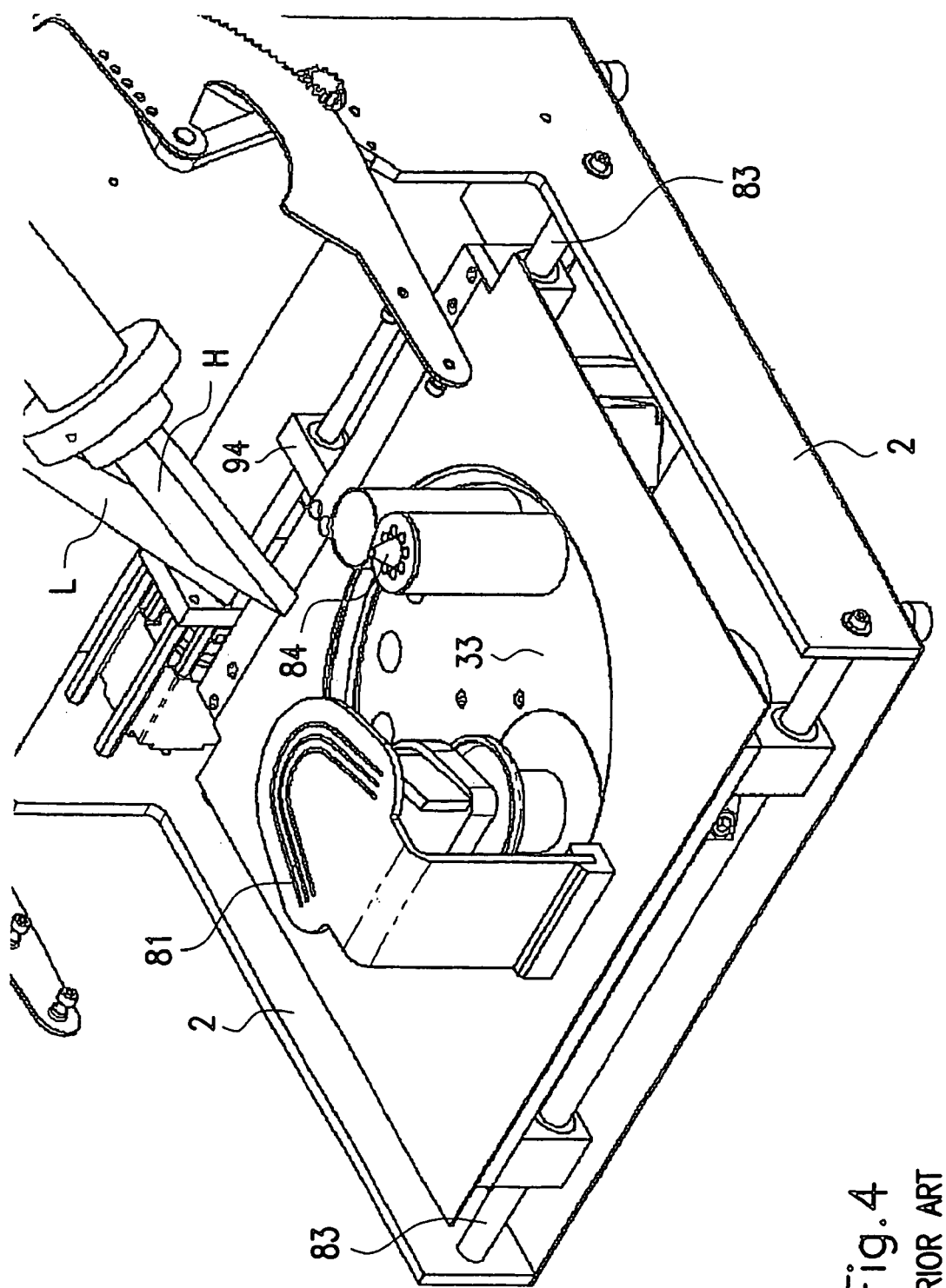
FIG. 4 is an enlarged presentation of a part of FIG. 3.

FIG. 3 and FIG. 4, a larger representation of part of FIG. 3, show a surface mapping device 1 with laser optics 4, from which a laser line L originates. The intersection of the laser line L with the rectangular field of view F originating from the objective defines the measuring field F. Each object to be measured must be passed through this measuring field F. This detail also applies to the configurations of FIGS. 5, 6 and 7, even if it is no longer shown there in order to illustrate the other features. To avoid repetitions, this was no longer mentioned in the discussions of FIGS. 5, 6 and 7 below; the use of this technique there, however, will of course be recognized and understood by a person skilled in the art.

To avoid repetitions, the discussion below will also refer to FIGS. 5, 6, and 7, insofar as the configuration is identical or comparable.

Figure 5:
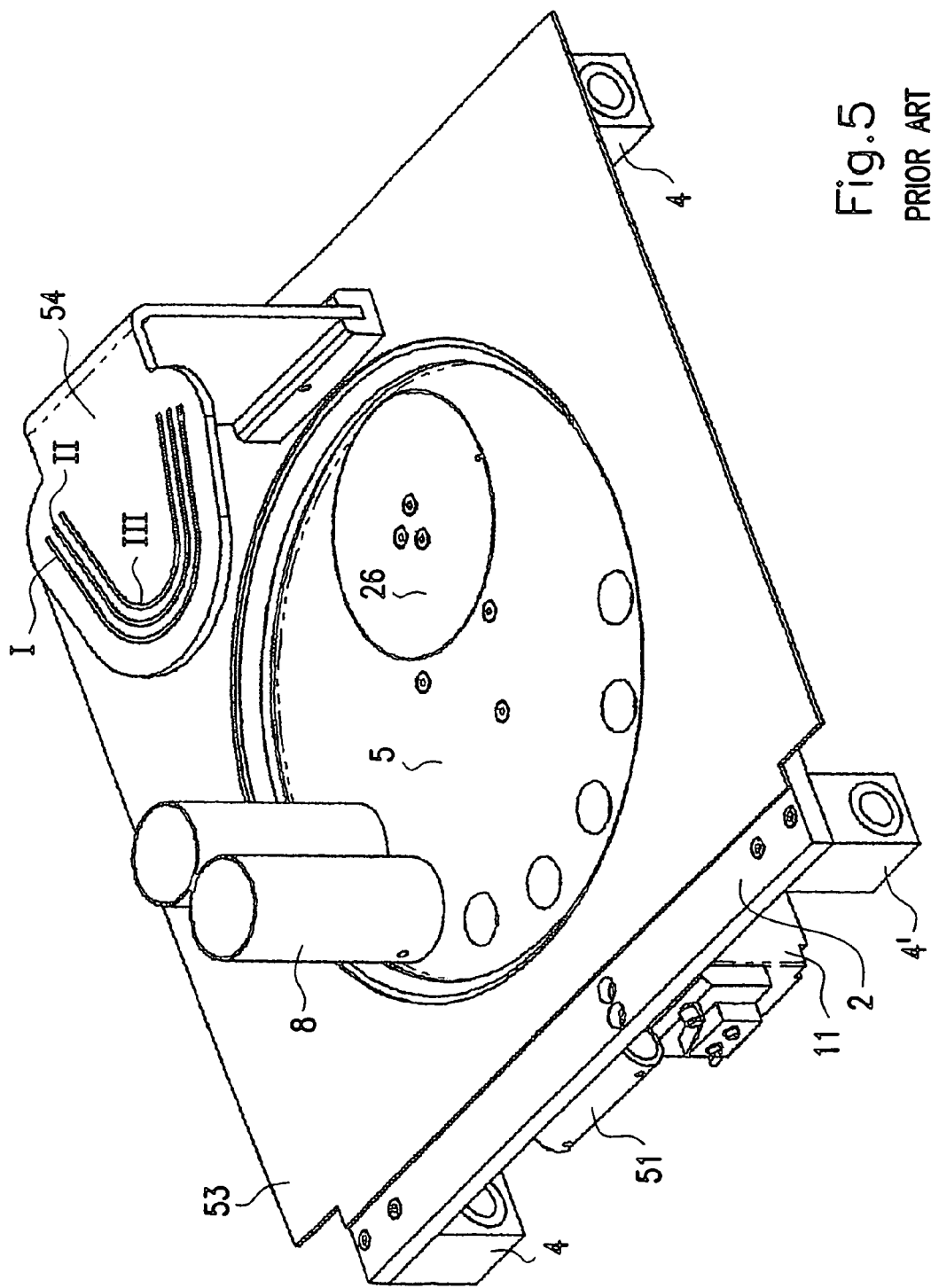
FIG. 5 is a schematic perspective view of the embodiment of the surface mapping device from FIG. 3 from above at an angle, in a different setting and enlarged.
Figure 6:
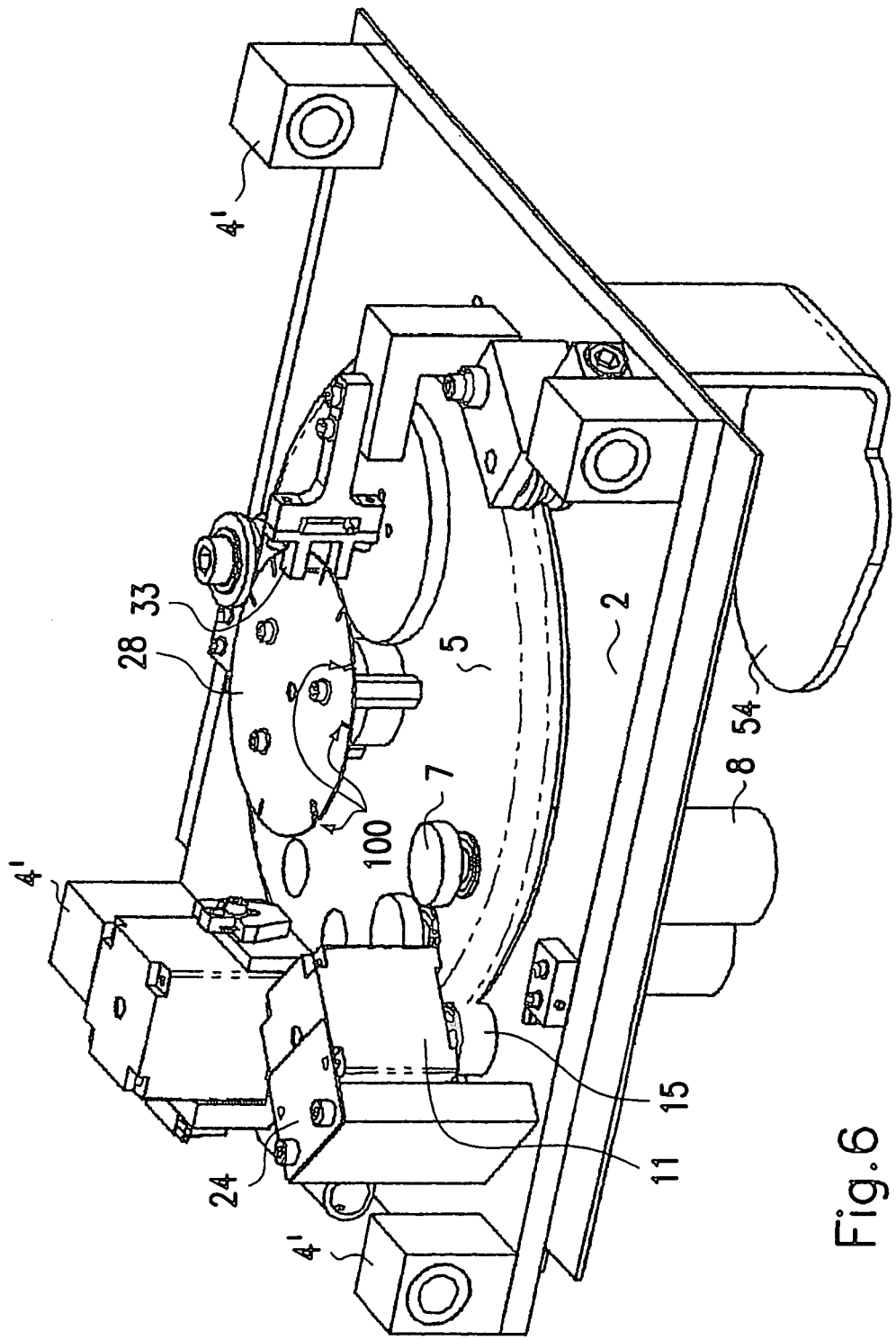
FIG. 6 is a schematic perspective view of the embodiment of the surface mapping device from FIG. 3 from below at an angle and enlarged.

The "traversing" of measuring field F is implemented by means of a linear guide 83 (or reference number 4' in FIGS. 5 and 6). To be able to position several individual objects, such as, in particular, teeth, within the measuring field, a rotary table 33 (or reference number 5 in FIGS. 5, 6, and 7) rotates from measuring pot 84 to measuring pot 84 (in FIG. 5, the measuring pots are labeled by reference number 8). In FIG. 3, only two measuring pots 84 are sketched in by way of an example (in FIG. 5, e.g., only two measuring pots 8 are likewise shown), but a total of, for example, seven could be mounted.

Once a measuring pot 84 (or 8 in FIG. 5) holding a tooth arrives in the measuring field, the large rotary table 33 (or 5 in FIGS. 5, 6, and 7) stops rotating. Thus, rotary table 33 (or 5 in FIGS. 5, 6, and 7) only serves to position the pots 84 (or 8 in FIG. 5) holding the individual teeth and/or a jaw, which will be explained in greater detail below. As already explained above, the measurement as such is carried out by means of a linear movement of measuring table 53 on the linear bearings 83 or 4' (FIG. 5).

The result is a measuring line that can see only one side of the tooth to be surveyed. To be able to obtain additional measuring lines from additional angles, pot 84 (or 8 in FIG. 5) located in the measuring field can be rotated around its own axis between the individual measurements. This results, for example, in eight views, or, in other words, pot 84 (or 8 in FIG. 5) is rotated by 45° around its own axis between measurements. Thus, in such a case, there are eight measuring lines from different views. Portions of the thus obtained surface data occur in several measuring lines. By means of these overlapping areas, suitable means or methods in the form, for example, of an already-explained matching software can assemble the individual measuring lines into a complete 3D surface image of a single tooth with a high precision of measurement.

With these data it is now possible to mill the inside data record of a dental crown. In addition to milling individual crowns, several single teeth can also be combined to form a bridge. To be able to mill bridges, the spatial position of several single crowns relative to one another must be determined as fast as possible. For this purpose, a complete jaw model is surveyed in the same way as a single tooth. It is placed on an additional rotary table 26 which is provided in rotary table 5 of FIG. 5.

Figure 8:
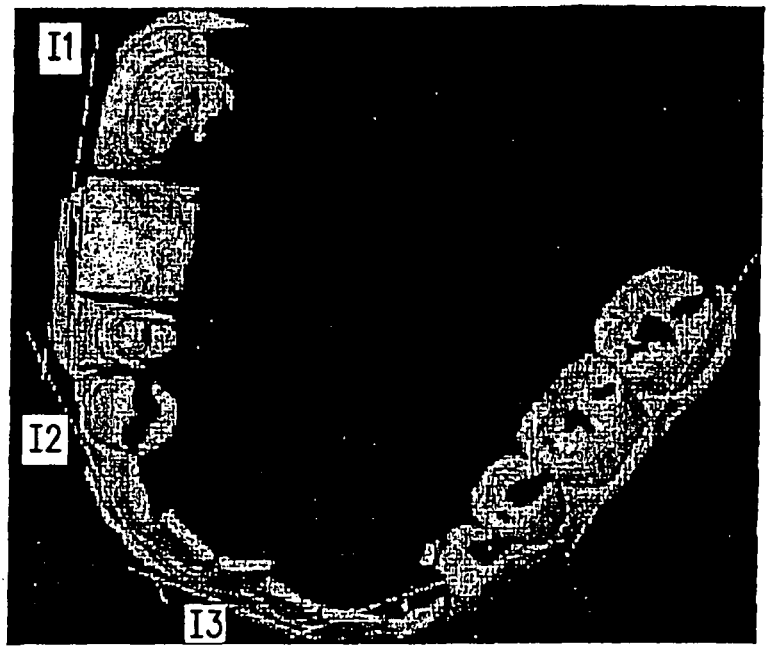
FIG. 8 is a graphical representation of a jaw with schematically drawn-in positions of measuring strips on the basis of data scanned in according to WO 02/39056 A1.
Figure 9:
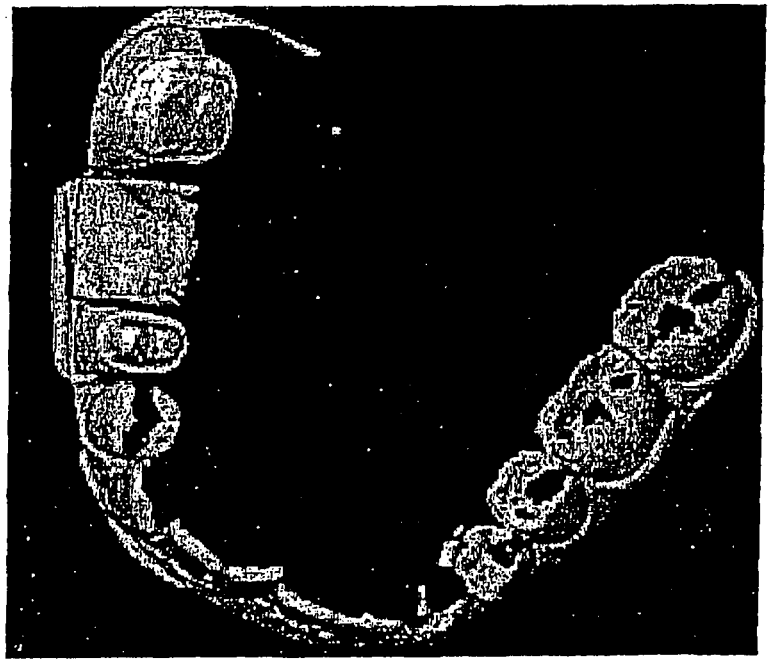
FIG. 9 is a graphical representation of the jaw from FIG. 8 with teeth processed according to WO 02/39056 A1.

The result can be seen in the image of FIG. 8. The direction of the measuring lines is illustrated by five white lines (the labels I1, I2 and I3 are indicated for the sake of example, and otherwise only the lines are drawn in). This measurement result does not include all data of the jaw, but sufficient data for the outer surfaces are available to be able to produce them automatically with the data of the individual dental stumps.

Subsequently, a software search which leads to an agreement of the data begins with suitable devices or methods. The result can be seen in the image of FIG. 9. The two highlighted data records of the first tooth at the top of the left side and of the next tooth in the jaw model following the gap represent the referenced single teeth.

Additional improvements will be illustrated and explained below.

Figure 7:
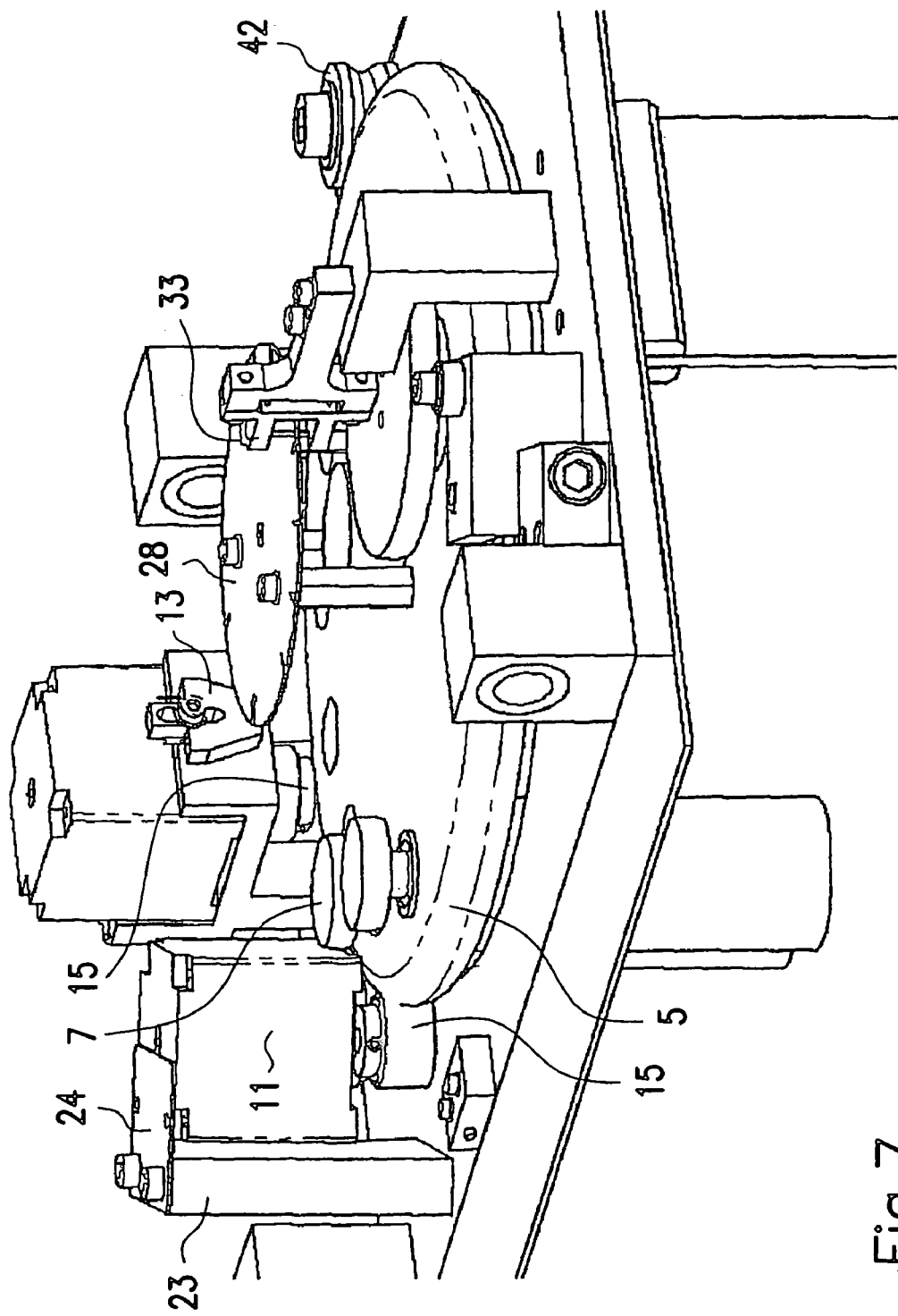
FIG. 7 is a schematic perspective view of the embodiment of the surface mapping device from FIG. 3 from below at an angle and enlarged, as well as rotated somewhat with respect to the view from FIG. 6.

With reference to FIGS. 5, 6, and 7, of which FIG. 5 is a perspective plan view and FIGS. 6 and 7 are perspective views of the same device from below, a rotary table 5 serves to transport various measuring pots 8 for single teeth under the laser measuring arrangement (cf. FIG. 3). This rotary table 5 is driven by means of a friction wheel 15 (see FIG. 6). The front of this friction wheel 15 is pressed against rotary table 5 by means of a spring plate 24 (see FIG. 6). Thereby any potential wear of a rubber surface or of the rubber material of friction wheel 15 is compensated.

The position of rotary table 5 is determined by means of an encoder disk 28. In the present case, the disk is constructed in the form of a metal sheet 28 (see FIG. 6) which has slots 100 precisely at those points in which the required stop positions are located. The slots 100 are detected by means of a light barrier 33 (see FIG. 6). In a suitable device or by means of a method, a control software evaluates the light barrier signals and starts and stops the table or plate 5. Rotary table 5 has seven positions/pots for single teeth. If a job is to contain more than seven preparations/teeth (a maximum of 14 teeth per jaw is possible), the job can be scanned in 2 batches.

Advantages of the devices described above:
extremely favorable production costs
available anywhere
no wear and tear
quiet operation
exact knowledge of position As an alternative to friction wheel 15, it is also possible to use, for example, a belt pulley or a toothed belt.

The construction of the frame can be made more economical by additional measures. For this purpose, the frame of the equipment/device is suspended on two guide rods 83 (cf. FIGS. 3 and 4). Thus, the complete frame of the apparatus consists only of two lateral parts 2 (cf. FIGS. 3 and 4), the guide rods 83 (cf. FIGS. 3 and 4), and an optical plate (FIG. 5). Inaccuracies caused by the mechanical construction of the linear rod guide are compensated for by the software (e.g., by means of so-called "look-up tables"). A precision spindle 94 (cf. FIGS. 3 and 4) is attached to the side of the moving table on which the laser arrangement is located. Thus, angular errors of the spindle have less of an effect. Advantages of this configuration include low production costs, high precision, a markedly lower transport weight, and a more compact construction.

Another improvement with respect to prior art before WO 02/39056 A1 can be undertaken to protect the laser diode electrically. For this purpose, the laser optics, the laser diode, and the electronic drive for the laser diode are housed together in a metal housing. This provides as advantages an improved protection of the diode, in particular against electrostatic charges from the outside, and a rapid exchange of parts during repairs.

In addition, other improvements according to WO 02/39056 A1 over and against prior art are possible in the manner in which jaw models are adjusted. To be able to optimally adjust jaw models that are to be surveyed, a template 54 (see FIG. 5) is needed. Since there are jaw models with different diameters (e.g., for children and adults), the jaw model must be adjusted to the size required. For this purpose, for example, 3 different adjustment contours I, II, and III are engraved or otherwise suitably placed on the transparent Plexiglas disk from which template 54 is preferably made.

Furthermore, improvements are possible, for example, with regard to the rotation of the individual pots by 45o. Rotary table 5 (FIGS. 5, 6, and 7) transports individual pots 8 to the measuring position in front of the friction wheel 15. While rotary table 5 is moving, frictional contact between the pot 8 and the friction wheel 15 is automatically generated. The novelty is that friction wheel 15 consists of rubber or at least has a rubber bearing surface while the opposing wheel 7 is made of solid metal. Advantages include a reduction in price, easier manufacture, and longer service life.

Another aspect of WO 02/39056 A1 will be explained by reference to FIG. 10. This figure shows 3 dental stumps 101, each consisting of a ground portion 101a and a residual tooth portion 101b. The grinding is done manually by a dentist and necessarily leads to undercuts 102 which, when several adjacently positioned individual teeth or their stumps 101 are observed, differ in shape, position, and size.

To construct a planned prosthesis 103, the overall contour of which is shown as a broken line by way of an example only on stump 101 at the far left side of FIG. 10, on dental stumps 101, a so-called cap 104 is first produced for at least one stump 101; it can, as a rule, be slipped over stump 101 in exactly one placement or push-on direction as indicated by arrow E. It is not possible for cap 104 to fill the undercuts 102 since otherwise the cap could no longer be slipped on. In the case shown in connection with the present embodiment, 3 stumps 101 are located side by side, and the 3 caps 104 thereon are combined to form a bridge by connecting each adjacent cap 104 by means of a web 105.

In designing the totality of all of caps 104, it is necessary to determine an optimum placement or push-on direction which minimizes undercuts 102 which are also formed, for example, because of the oblique position of one stump 101 relative to the other stumps 101, as is illustrated by stump 101 on the right side of FIG. 10.

This can be carried out in advance on the basis of the 3D data obtained from stumps 101. For this purpose, as already explained in detail in the present documents, a 3D data record is generated by scanning as disclosed in WO 02/39056 A1 and is used for model calculations to identify the optimum placement or push-on direction. For this aspect of the method according to WO 02/39056 A1, different push-on directions are successively used as a basis, and the "dead space" caused by the undercuts 102 is determined for each of the results. The optimum placement direction A is obtained by identifying the variation with the smallest "dead space."

Especially as a result of an oblique position of a remaining stump 101, but also as a result of other inaccuracies in the work of the dentist, it is possible for cases to arise in which a cap, relative to a residual tooth region 101b, would have to have a wall thickness of 0 mm in certain places. In such a case, it is fundamentally impossible to produce a dental prosthesis. In order to proceed further, expensive and time-consuming work must first be carried out on the tooth stump 101 involved, and often it is not certain that this work will lead to a useful result.

In addition to the optimization of the placement direction E to minimize the undercuts or "dead spaces" 102 as provided by WO 02139056 A1, WO 02/39056 A1 can be used to further improve the procedure for producing dental prostheses. By means of the mapped (scanned) 3D data, it is possible to prepare recommendations for the treating dentist which tell him what kind of work should be done on the dental stumps that would more likely lead to an improvement of the fit and stability of the prosthesis to be manufactured, including what to do to markedly reduce the undercuts or "dead spaces" 102. For this purpose, the scope of the method according to WO 02/39056 A1 is extended so that relative to a recorded 3D data record of one dental stump 101 or a combination of several dental stumps 101, an optimum push-on direction for cap 104, in particular a combination of a plurality of caps 104 to form a bridge 106, is calculated, provided that changes in the shape of the dental stump/the dental stumps 101 are possible. Thus, the method and system of WO 02/39056 A1 serve not only to allow an adjustment to a given situation when caps 104 or bridges 106 are produced and pushed on but also to change the existing circumstances so as to optimize the result, i.e., the prosthesis. For example, the method and system can provide for the inclusion of a graphic display of the stumps, including, for example, specially colored regions for the finishing work, which display can serve as a basis for a dialogue between a dental lab and a dentist.

Furthermore, WO 02/39056 A1 with its above-explained embodiments also advantageously creates the possibility for quality assurance, including, in particular, the possibility of unambiguously assigning given treatment results to the dentist who prepared the dental stumps by means of grinding or to the dental lab which produced the caps/crowns/bridges. Thus, it will be possible for the first time to settle questions of who bears the responsibility in cases of an inaccurate fit. Furthermore, it will be possible to advantageously make use of the fact that all data at the outset of a treatment as well as all data of the dental status at certain intervals can be continuously archived in an especially simple and at all times readily accessible manner.

The method and its variations explained above with reference to FIG. 10 are equivalent to appropriately constructed devices by means of which these methods can be carried out so that even those devices with which the person skilled in the art would be immediately familiar on the basis of the representation of the methods in their general and specific embodiments are deemed to have been disclosed in the present documents.

Another aspect of WO 02/39056 A1 relates to the automatic generation of the masticator surface of a dental prosthesis, taking into consideration the opposing bite (upper jaw to lower jaw). In the embodiment illustrated in FIGS. 11 and 12, the following steps described below are provided:

1. Insertion and calibration of upper and lower jaws 206 and 207 in a mastication simulator or articulator 200 with adjusting joints 201 until the bite situation is simulated, as shown in FIG. 11. Supports 202/202a and 203/203a for upper and lower jaws 206 and 207, respectively, have a detectable spatial position. Supports 202/202a and 202/203a, for example, respectively have a defined zero position or a zero position with respect to each other. Each support 202/202a and 203/203a has two parts and consists of a supporting base 202a and 203a, each of which is permanently affixed to articulator 200, and a jaw support 202 and 203, to which upper jaw 206 and lower jaw 207, respectively, is attached.

2. Reading in/recording, e.g., 6 degrees of freedom: 2 possibilities:
   (a) reading a scale manually; (b) reading out of measurement sensors Using articulator 200, the optimum/correct position of supports 202/202*a* and 202/203*a*, i.e., actually of the support bases 202*a* and 203*a*, is determined, taking into account upper and lower jaws 206 and 207, respectively, as shown in FIG. 11. This can take place automatically on scales (not shown) which are provided on and are attached to articulator 200 or by means of position and phase-angle sensors (not shown). It should be noted that articulator 200 preferably allows an alignment of upper and lower jaws 206 and 207 with respect to each other in preferably six degrees of freedom.

3. Insertion of the respective jaw support 202 or 203 with the upper jaw model 206 or the lower jaw model 207 into a support 205 analogous to the support bases 202*a* and 203*a* of scanner 204 according to FIG. 12, with the spatial position of support 205 relative to the measuring system or the data system of scanner 204 being known.

4. Referencing is then carried out by means of software.

5. Proposal for the masticator surface (e.g., incisor) from the database
   Automatic adaptation of the database model to the opposing-bite situation
   Search for contact points with envelope data
   Matching the masticatory surface to the internal data record
   Alternatively: acquire the position of the jaw in an "articulated" manner by scanning a portion of the articulated jaw and subsequently match the data of the upper and the lower jaws with these partial data records to produce the bite position.

The aspect of WO 02/39056 A1 explained with reference to FIGS. 11 and 12 is also to be considered as having been disclosed as a method and as a device, since a person skilled in the art can recognize suitable devices in general or special embodiments from the explanations above.

The present invention will be explained in greater detail below with regard to its individual aspects, it being clear without further elaboration to a person skilled in the art which statements and representations are to be understood as being merely for the sake of example. Furthermore, a person skilled in the art will recognize, without specific representations, advantageous combinations of the details below, as well as their designs and effects, in an overall view and also in conjunction with the above-described prior art, to that extent also illustrated in the drawings, which prior art is likewise a part of the disclosure of the present documents. Moreover, the analogies between devices and methods according to the present invention are clear to a person skilled in the art, without the necessity for separate descriptions and illustrations in each case for devices and methods that serve the same purpose. It is essential, however, that the individual aspects of the invention presented below need not necessarily be combined with the above-discussed prior art, above all, WO 02/39056 A1, but can be implemented with any suitable technology. Thus, surface mapping methods employing mechanical scanning, other optical scanning systems and methods and any other type of suitable scanning technology can be combined with the individual aspects of the present invention. For material machining, particularly in regard to the formation of denture parts, other technologies besides milling, such as casting techniques, laser sintering and so on may be utilized in connection with the individual aspects of the present invention.

According to the invention, the first aspect of the present invention creates, in particular, devices and methods for partially or fully automatic edge recognition of inlay preparations and, even further, for the production of inlays as denture parts. A corresponding device is immediately evident to the person skilled in the art from the presentations below and the figures of the drawing cited therein.

Figure 13:
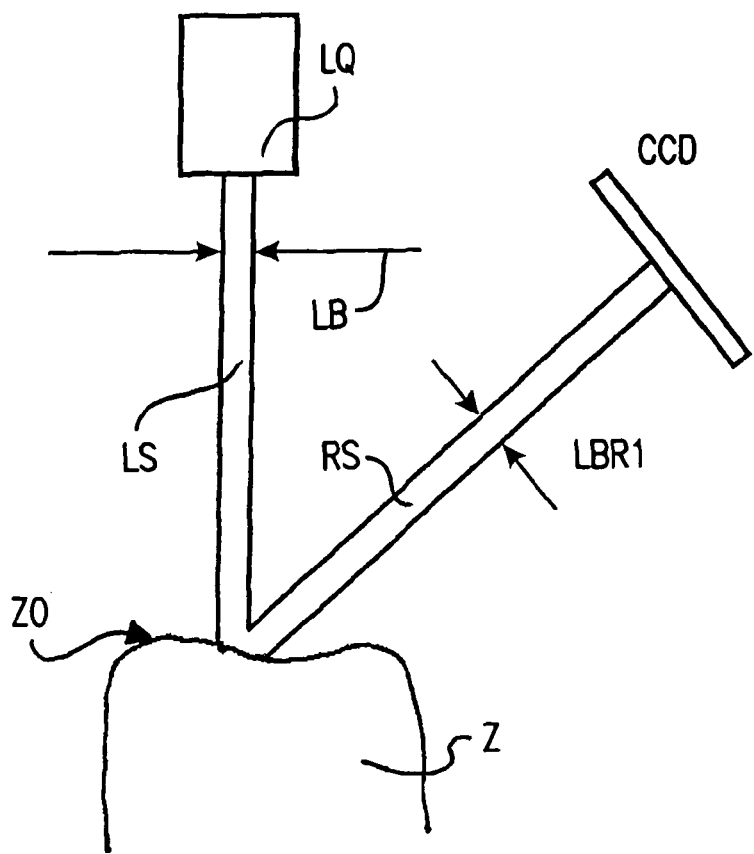
FIG. 13 is a schematic view of one embodiment of a surface mapping device according to WO 02/39056 A1 while scanning a complete masticatory surface of a tooth, as well as a sketch of a measurement signal resulting therefrom.
Figure 13:
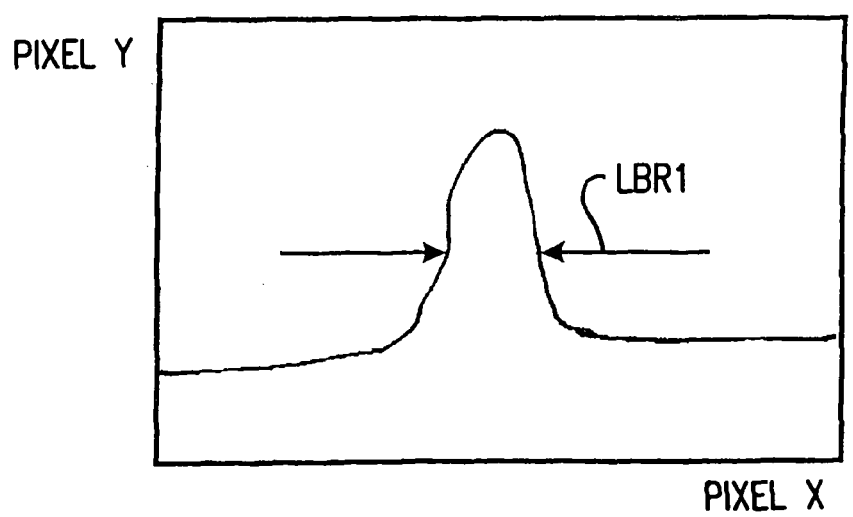
Figure 14:
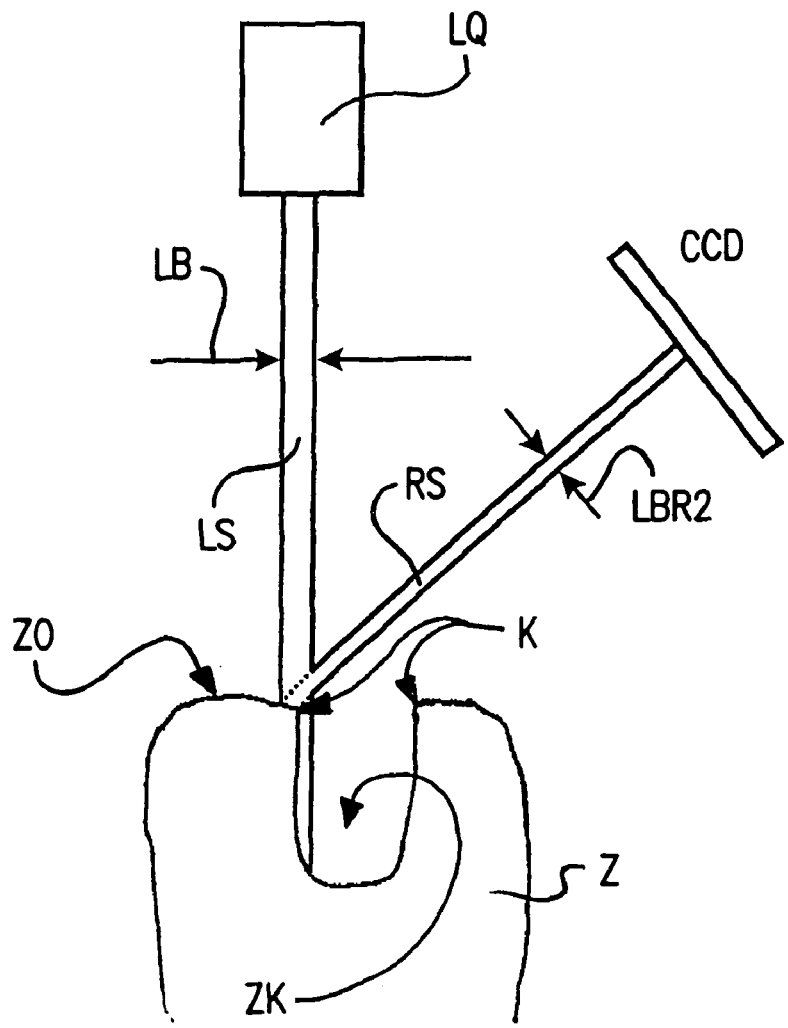
FIG. 14 is a schematic view of one embodiment of a surface mapping device according to WO 02/39056 A1 while scanning a masticatory surface of a tooth with a hole for insertion of an inlay, as well as a sketch of a measurement signal resulting therefrom when scanning at the edge of the hole.
Figure 14:
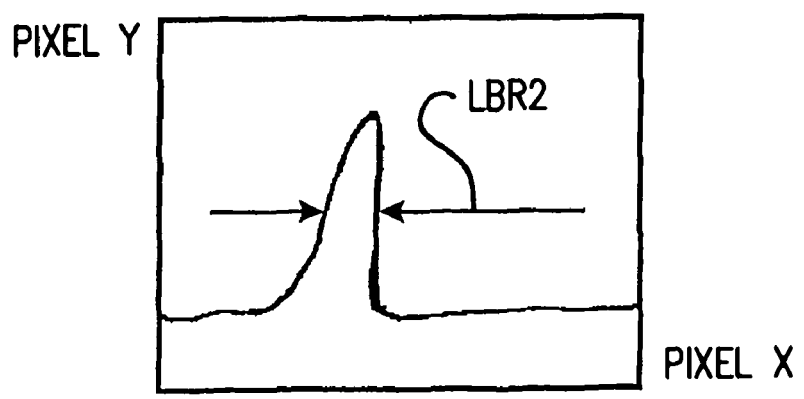

In the production of the aforementioned denture parts, namely dental inlays preferably, with other denture parts of a related nature also covered, by means of the CAD-CAM method, there is the particular difficulty of analyzing by means of software a 3D surface data record of a tooth stump prepared by the dentist for an inlay such that the software automatically recognizes where the boundary runs between the inlay to be prepared and the remaining tooth substance. For an inlay preparation, the sharp edge of the preparation is characteristic, as is illustrated by the comparison of FIGS. 13 and 14. The method according to the invention described below as well as the device that is clear without further elaboration to a person skilled in the art contains an automatic recognition and separation of this boundary.

Figure 15:
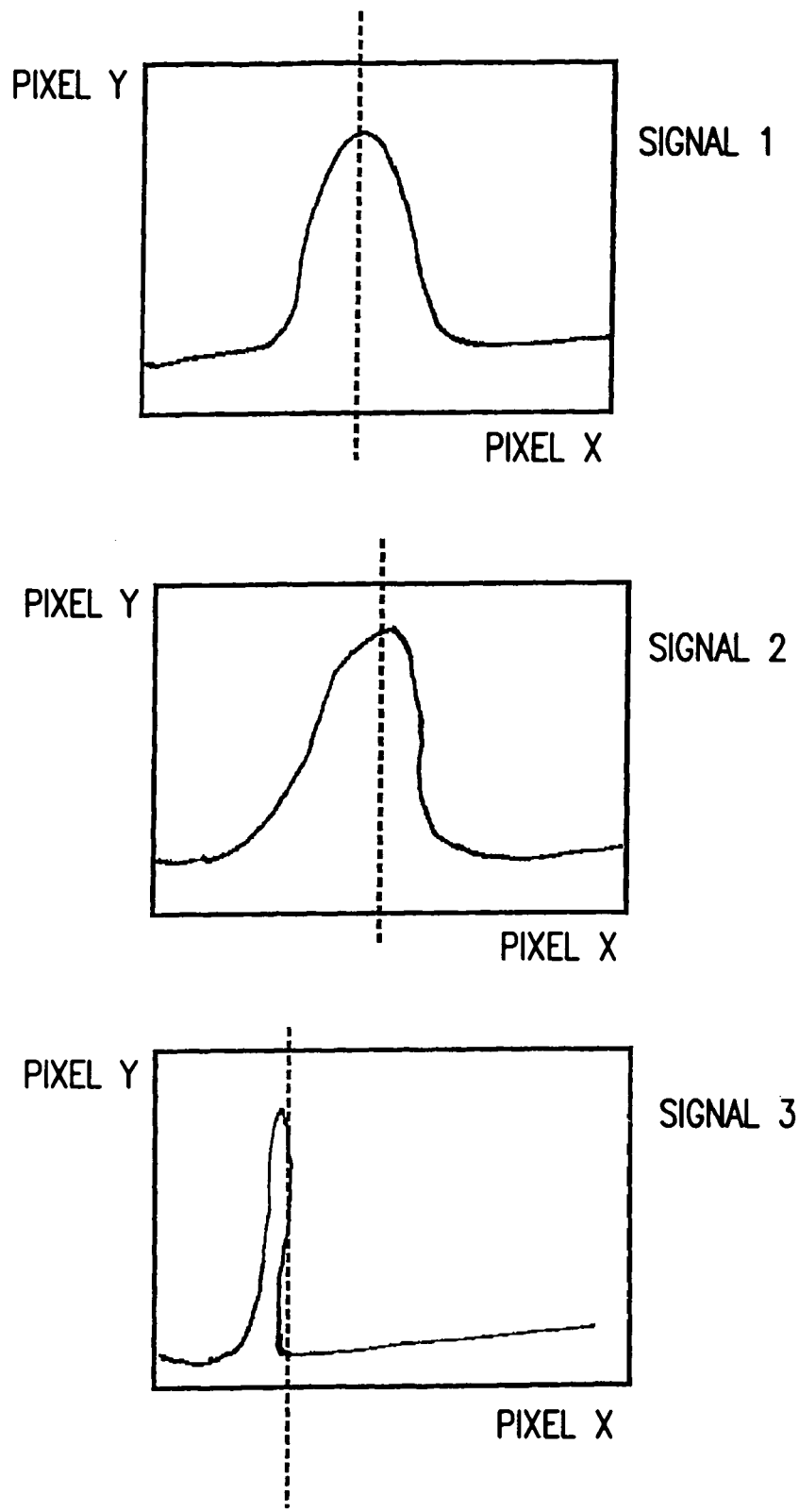
FIG. 15 is a schematic representation of examples of signal forms of a signal 1 that originates from the scanning of a surface, of a signal 2 obtained when the edge of a hole in the surface is reached and of a signal 3 that is obtained directly at the edge of a hole in a surface.

Already in a measuring method with a laser as in prior art according to WO 02/39056 A1 or DE 19721688 A1, the light signal on the camera chip that is to be analyzed contains information that is essential to the above-described method: while the laser line contacts a surface part that contains no edge, as illustrated in FIG. 13, the full width of the laser beam is reflected. FIG. 13 shows a tooth Z with a tooth surface ZO, on which a laser beam LS from a laser light source LQ with a beam width LB is incident. The reflected beam RS has a width here of LBR1, with which it strikes a CCD-chip CCD as the detection device. In the case where laser beam LS strikes an edge, as is visible from FIG. 14, only a partial width LBR2 of the beam LS is reflected as reflected beam RS to the CCD-chip CCD. As an example in relation to the situation of a reflection without an edge, the width LBR2 of reflected laser beam RS reflected at an edge K is equal to ½ LBR1, as the representations of the corresponding situations in the lower halves of FIGS. 13 and 14 illustrate. The shape of the signal to be analyzed likewise changes, as the representations of the corresponding signals in the lower halves of FIGS. 13 and 14 illustrate. While a, symmetrical Gaussian curve is described for the surface (cf. FIG. 13), the signal in the area of an edge has an asymmetrical curve (cf. FIG. 14), as can be seen in FIG. 15, in which are sketched schematically the signal forms of a signal 1 that derives from the scanning of a surface (analogous to FIG. 13), of a signal 2 that is obtained upon reaching an edge of a hole in a surface, and of a signal 3 that is obtained directly at the edge of a hole, or more particularly here, a tooth cavity ZK in a surface (analogous to FIG. 14). The information from the change in width and form of a signal can be processed for optimal determination of the actual periphery of edge K. By repeatedly surveying this edge K from several solid angles with the above-described methods, these readings can be checked against one another and be established in their final form by averaging in the edge area.

Figure 16:
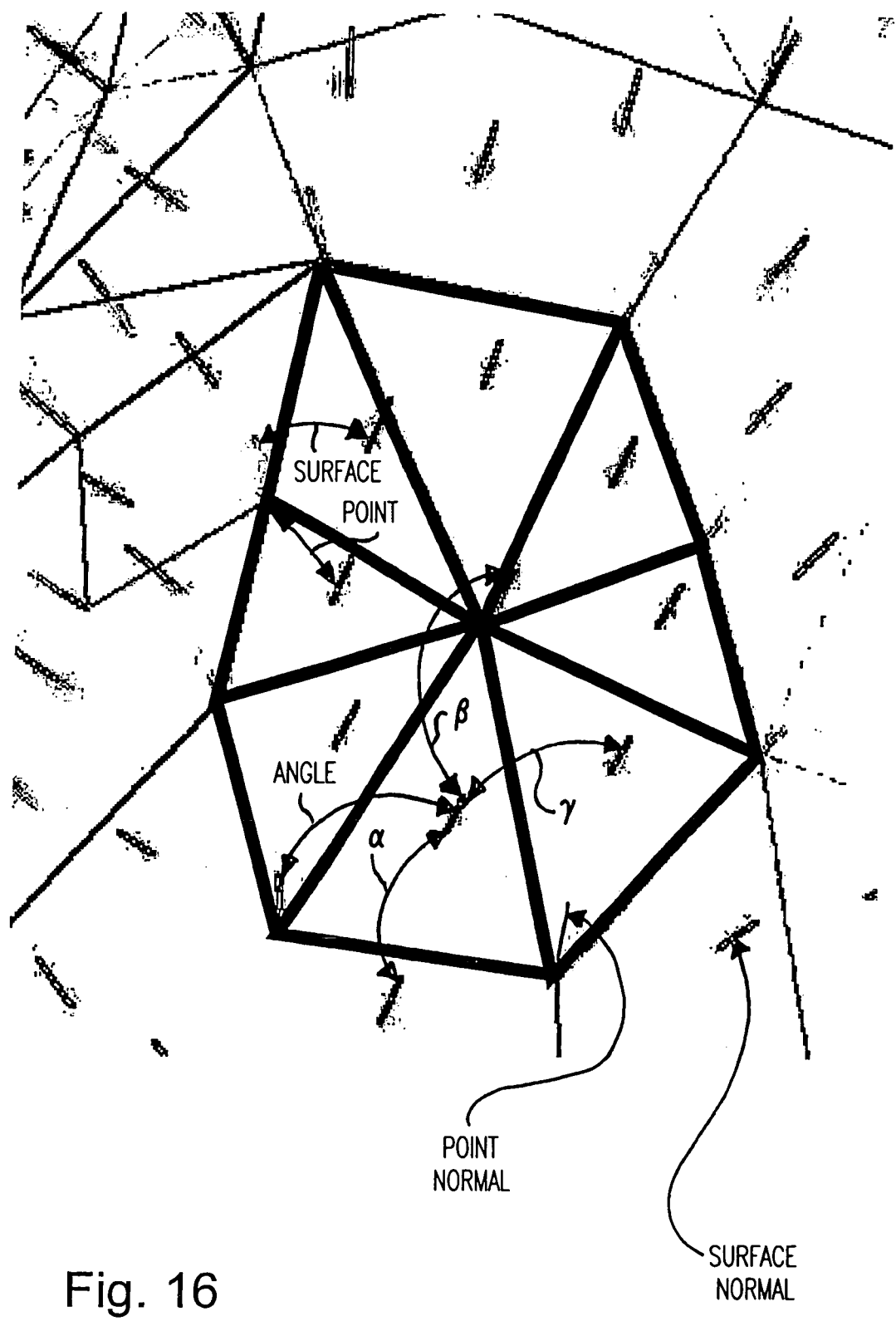
FIG. 16 is an example of a graphical representation of measurement results from a mapping of a tooth surface.

A 3D data record scanned in this manner of, for instance, an inlay cavity, which 3D data record was further processed by, as one example, surface triangulation methods, typically contains surfaces which are described by at least three or more [sic] vertices. These surfaces are connected by shared edges or points, as is illustrated in FIG. 16. The described method for partial or fully automatic edge recognition and separation is now accomplished by the a-priori information that edges of preparations have much greater-than-average curvatures or angles.

If, at all points of the surface data records, the average point normals from all adjacent data records are calculated, then a significance for the curvature can subsequently be defined by a difference analysis of the point normal from the normals of the surface data record. By finding adjacency relationships, the following step attempts to increase the significance with respect to various criteria and to classify it. For instance, the adjacency relationships with respect to a coherent line can constitute one criterion. With that, the foundation stone for automatic edge recognition has been laid.

Figure 17:
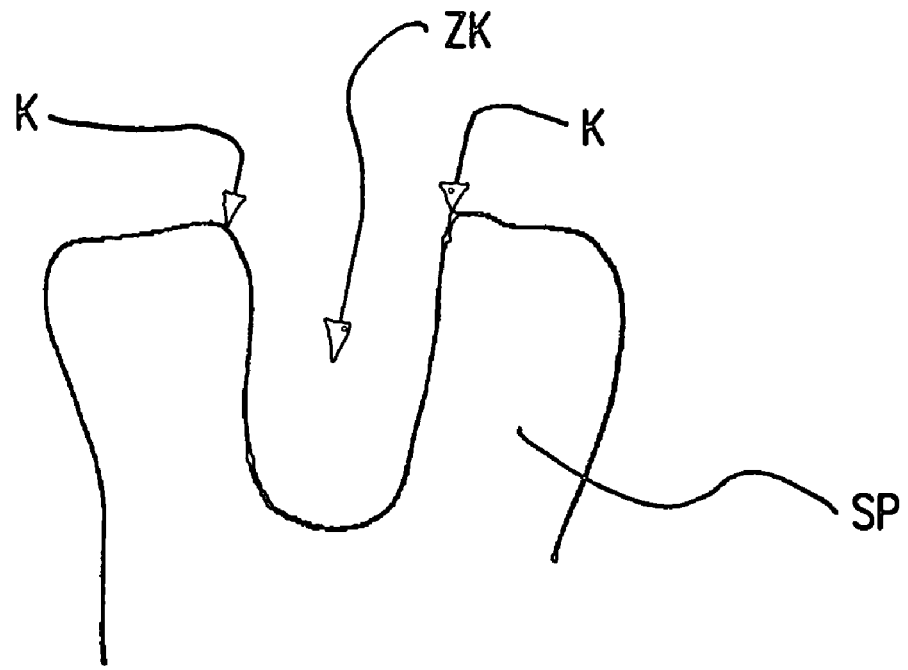
FIG. 17 shows schematic representations of two method steps in the production of an inlay according to one embodiment.
Figure 17:
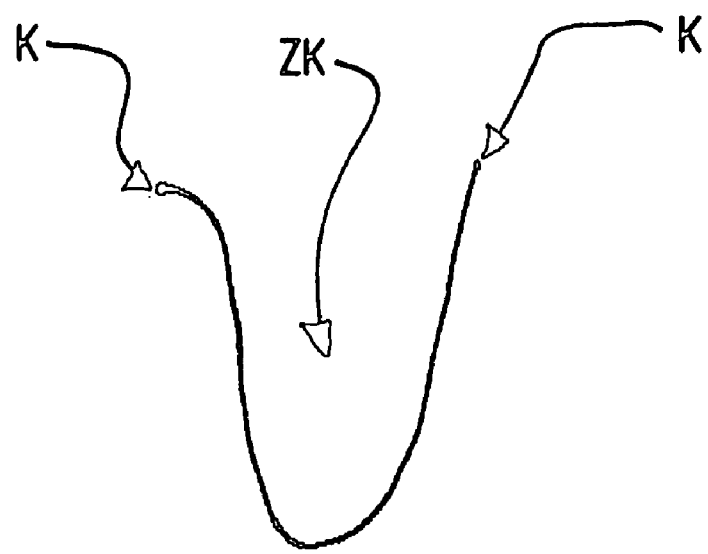
Figure 18:
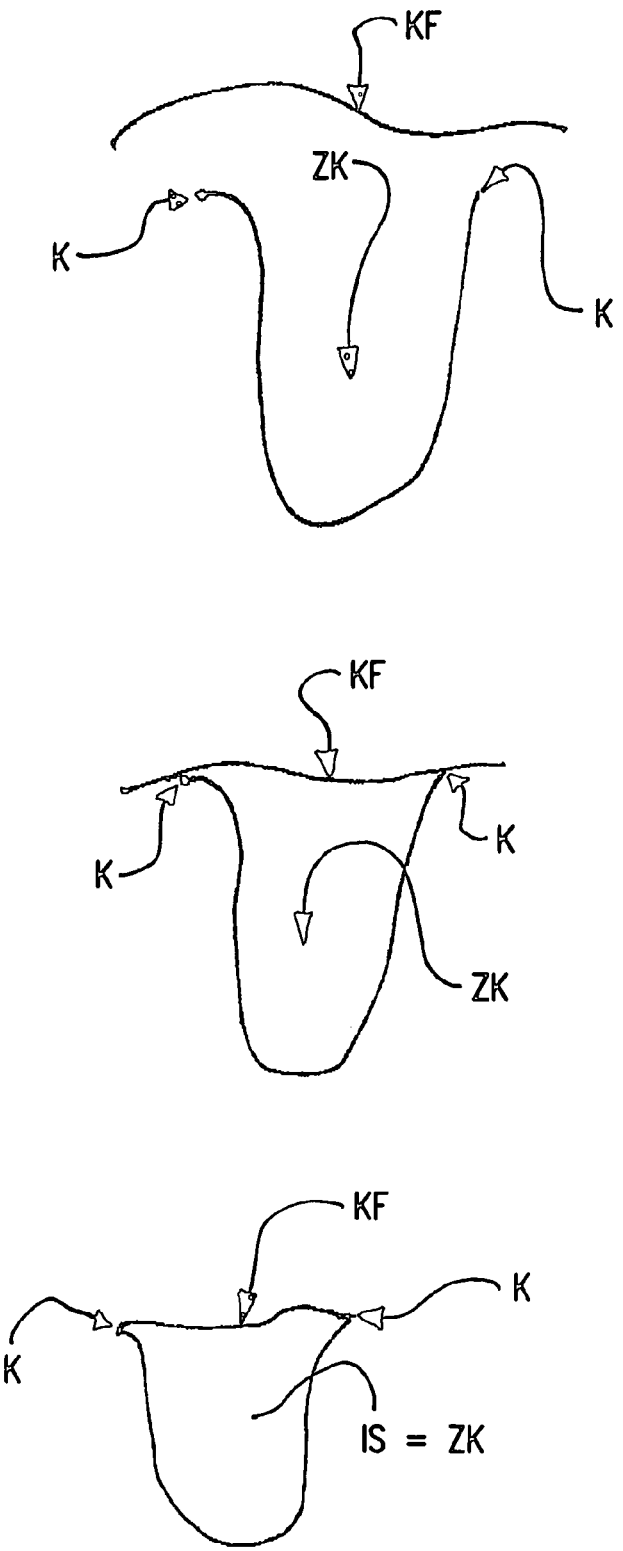
FIG. 18 shows schematic representations of three additional method steps in the production of an inlay according to the embodiment from FIG. 17.

By means of software, the edges can now be analyzed, recognized and assembled into a coherent edge profile, as is schematically shown in the method step representations of FIGS. 17 and 18. Only the surface segments present inside an edge profile are employed for the subsequent production of a dental inlay.

Item (1.) in FIG. 17 shows, schematically and only in side view, a complete data record of a stump preparation SP with a tooth cavity ZK prepared for a dental inlay and its periphery or edges K, this being in reality, however, a 3D data record as a whole, i.e., a three-dimensional data representation of the stump preparation.

Item (2.) in FIG. 17 schematically illustrates the step of recognizing and separating the periphery or edges K, with the two-dimensional depiction again being representative of the 3D data record from step (1.). The edge detection is accomplished as explained and shown, for instance, in FIGS. 13-16.

Step (3.) in FIG. 18 is once again schematically shown as a two-dimensional representation of the complete 3D data record for the sake for simplicity, with the missing side of the later inlay that is to be produced being added, by, for instance, importing a database masticator surface KF, to the data for the prepared dental cavity ZK which determines the shapes and dimensions of the inlay in other respects. In this step, masticator surface data stored, for example, in a database (e.g., for the fourth molar, lower jaw) are imported into the overall data record, or the original tooth shape data scanned by the dentist before treatment are imported, or the surveyed shape data of a masticator surface modeled by a dental technician in wax specifically for this inlay are imported.

In step (4.) of FIG. 18, the data of the imported masticator surface KF are linked to the data for the prepared dental cavity ZK, which [linking] is once again shown on a two-dimensional schematic example as a representative of the respective 3D data records of masticator surface KF and dental cavity ZK. By means, for instance, of an automatic fitting function using, for example, a matching algorithm, the masticator surface data are optimally adapted and placed on the periphery.

Figure 19:
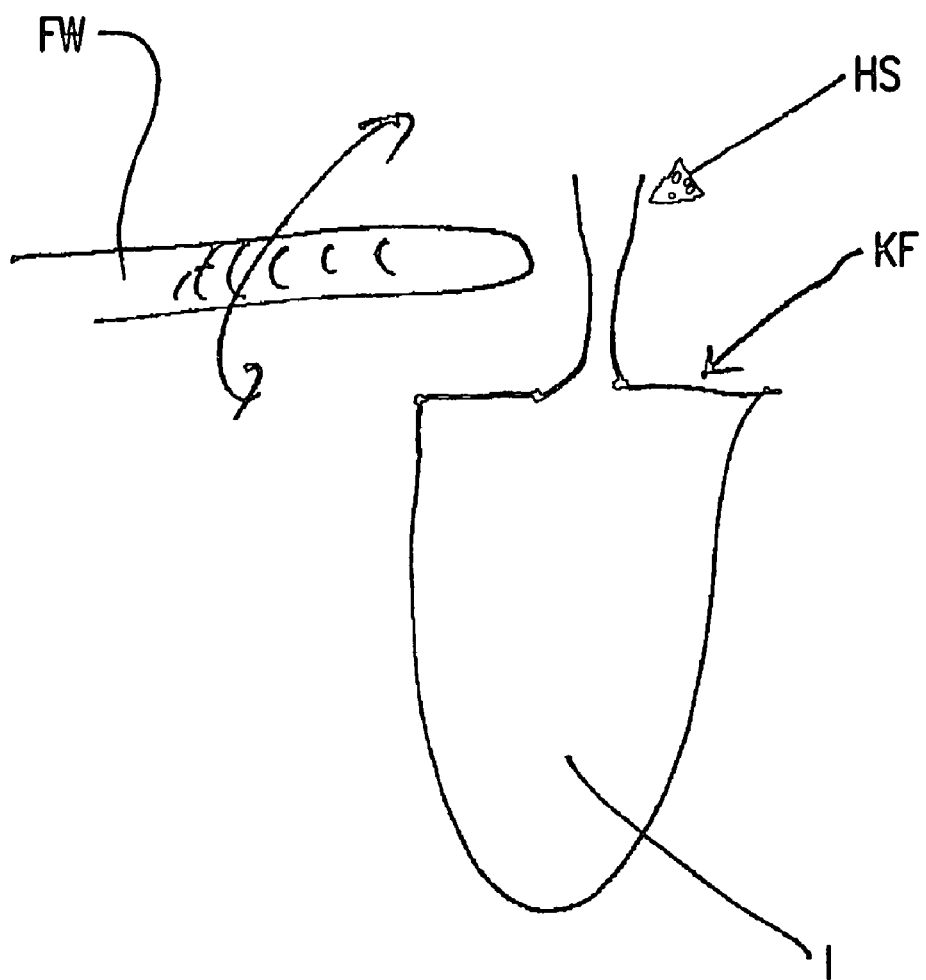
FIG. 19 is a schematic representation of yet another method step in the production of an inlay according to the embodiment from 17.

Finally, in step (5.) of FIG. 18 there is a morphing of the masticator surface and a separation of the excess, so that a finished inlay data record IS is obtained, which again is shown only for the sake of simplicity as a two-dimensional representative of the actual data record with the complete 3D data. For instance, the masticator surface can be adapted to the opposing bite by means of morphing. The resulting 3D data record can be used for CNC manufacture of inlay parts. It is particularly advantageous for the precision of the inlay I in this regard if, as shown in FIG. 19, the remaining handling web HS of the inlay I after completion of the grinding procedure with a grinding tool FW is positioned in the area of the masticator surface KF.

According to a second aspect of the invention, there is created, in particular, a method for producing complex denture designs. A corresponding device will be immediately evident to the person skilled in the art from the presentation below and the figures of the drawing cited therein.

Prefabricated parts are frequently used in conventional dental technology. Implantation abutments, other abutments and attachments, for example, are mechanically joined to the rest of the denture.

The invention makes it possible to eliminate the process of joining several prefabricated parts with, for example, adhesive. Besides saving money, this also yields an improved health compatibility for the patient, since only one material is introduced into the body. Additionally, a longer service life and a higher overall precision are possible.

A preferred component of the above-discussed aspect of the invention is that 3D CAD-CAM design data of a prefabricated denture part or of construction elements or connection elements of denture parts can be brought together with 3D measurement data of tooth stumps and/or tooth shapes (supra surfaces).

Figure 20A:
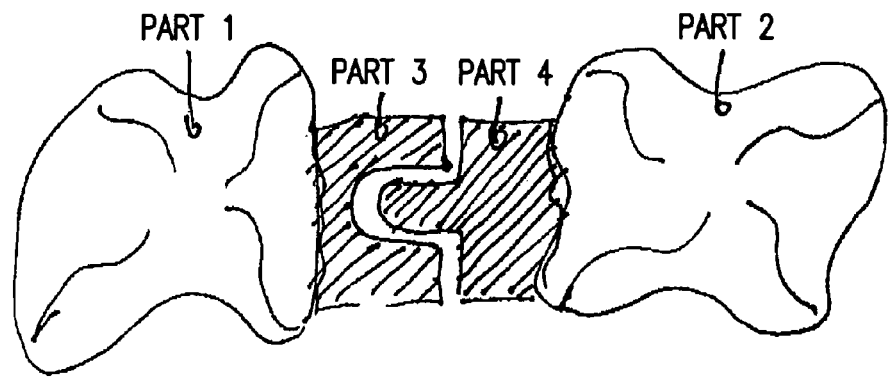
FIGS. 20a AND 20b are schematic representations of a simplification in the production of a denture according to another aspect of the present invention.
Figure 20B:
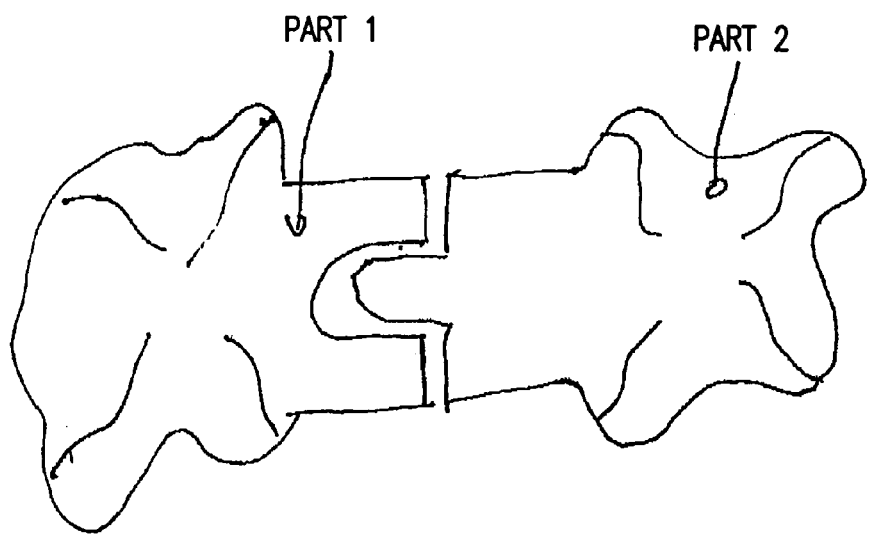

FIG. 20a shows by way of example a conventional final product situation and FIG. 20b shows a final product situation according to the present invention.

The method steps:
1. A preparation of a tooth stump or several tooth stumps or of a tooth or several teeth is surveyed and further processed by means of data technology into, for example, a triangulated surface model.
2. From a 3D finished part library, a design data set, such as an attachment part, an implantation abutment or other abutment is imported into the data record.
3. The measurement data of the tooth stump or tooth and the parts data of the prefabricated parts are assembled in software, taking into account the bite situation. This takes into account the facts of the patient's bite situation, particularly the so-called "placement direction." For instance, if several tooth stumps are to be taken care of by one bridge, then it must be possible for the bridge to be slipped simultaneously onto all the stumps.
4. The software can also be configured such that the design data (height and width, for example) remain variable.
5. After the measurement data and the design data have been brought together and redundancies have been deleted from the data records, the data can be used by a CNC milling machine for manufacturing. After the parts have been produced according to the above-described method, the finished product as in FIG. 20b is available.

The method can be applied so as to take into account the dental situation of the patient. Alongside measurement data of the jaw ridge, measurement data of adjacent teeth can be blended in.

A particular advantage of this method is that the placement direction can be taken into consideration in the design of attachments. The mixture of design data, CAD design tools, 3D matching tools and measurement data processing leads to a number of technical possibilities and process sequences.

Figure 21A:
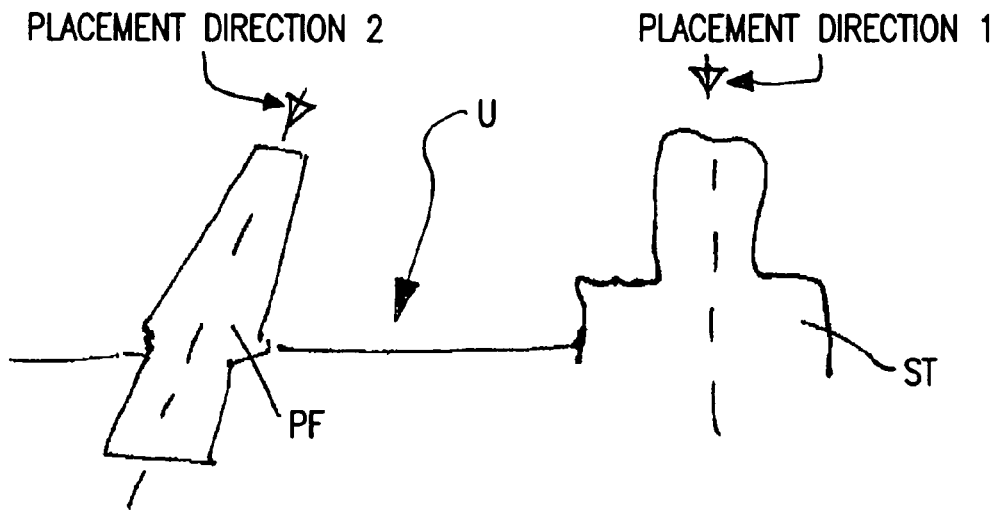
FIGS. 21a and 21b are schematic representations of a simplification in the production of a denture according to yet another aspect of the present invention.
Figure 21B:
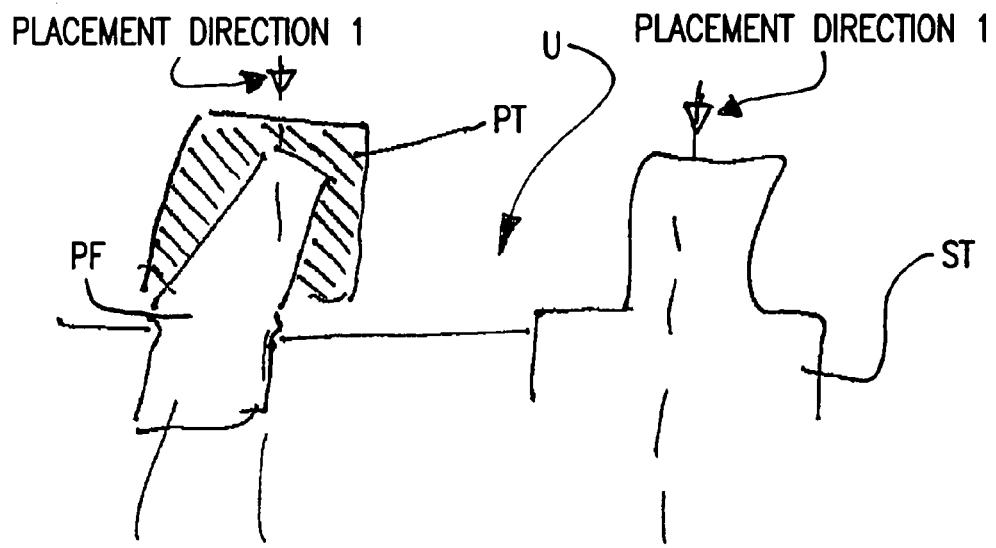

Another example of the invention is explained in FIGS. 21a and 21b as well as 22.

FIGS. 21a and 21b show an implantation abutment PF (with abutment), as well as a stump ST, which are to be jointly crowned by means of a bridge. For the sake of completeness it is also pointed that, instead of the implantation abutment PF, an additional stump can constitute the basis for the remaining procedure, or there can be more than two parts present, which can be arbitrary in nature, e.g., implantation abutments or tooth stumps. The situation is surveyed by prior art technology, in particular, according to WO 02/39056 A1, in order to obtain 3D data records of the implantation abutment PF in its position and of the tooth stump in its position and shape. If required, the shape of the implantation abutment can also be mapped, if it is not a prefabricated part whose 3D data are already in the system, so that only its position needs to be determined.

Figure 22:
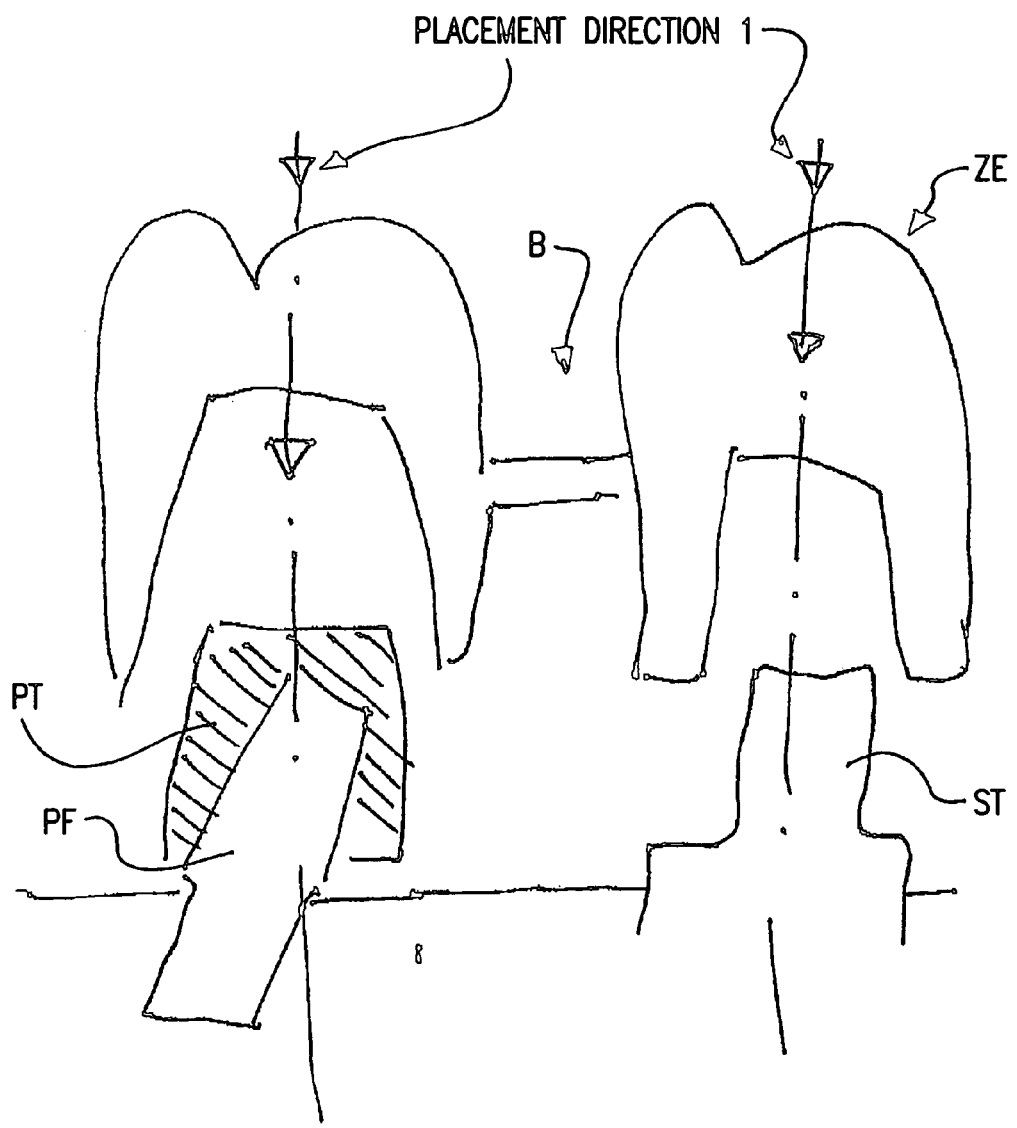
FIG. 22 is a schematic representation of the result of the procedure as in FIGS. 21a and 21b.

As is evident from FIGS. 21a and 21b as well as 22, however, there are two different placement directions here (placement direction 1 through stump ST and placement direction 2 through implantation abutment PF). In order to place a shared bridge on implantation abutment PF and stump ST or, for instance, on two stumps, a shared placement direction must be created. In FIGS. 21a, 21b and 22, placement direction 1 is selected for this purpose, which can be implemented fully automatically by means of the software employed, and can also be selected semi automatically within certain limits by an operator, due to selectability and adjustability in the software, and can be specified for the remainder of the procedure. In principle, a purely manual selection of the placement direction is also possible, which also enables a strong involvement of expert knowledge for complicated arrangements. Thus a proposal can be made completely automatically by the software, whereupon there can be a semiautomatic adaptation by a user within limits imposed by the software and finally, if no satisfactory or implementable solution can be achieved even with that, a purely manual specification can eventually be made.

By means of the knowledge of the placement directions, a software can calculate a primary part PT as in FIG. 21b, which acts as an adapter on implantation abutment PF in order to unite the two placement directions, so that placement direction 2 also applies to the latter. Boundaries for primary part PT or the adapter can either be set fully automatically by the softwarelor semi-automatically, in that certain boundaries are specified and adjustable within limits, or can be set manually, in that the boundaries are freely supplied by a user. In particular, the software can also immediately determine a milling direction for the denture part, specially as a function of the placement direction, and taking account overall of a wide variety of parameters.

Then, the measurement of stump ST including its environment U, in which the implantation abutment PF is located, is used as the inside data record. Subsequently, the design data record of implantation abutment PF (with abutment) is loaded and spatially correlated with the measurement data by means of matching methods. This serves to utilize the data of the design data record for the CNC manufacturing of the part, since thereby a higher precision of the final part can be achieved than in case of the processing of measurement data. The outer contour of the primary part can likewise be artificially generated or CAD-designed, with a placement direction or the placement direction 1 defined by stump ST serving as the basis. Thus an individual, mechanically precise primary part can be manufactured.

In the next work step, the primary parts and the tooth stump are measured together and the inside data for the denture parts ZE to be arranged thereon, such as a bridge B as in FIG. 22, are precisely determined. Besides a finished part database, masticatory surface databases can also be used for import and matched to and fused with the measurement data. An adaptation to the opposing bite is accomplished, for instance, by morphing. Thus an individual, highly precise and complex bite situation can be machined with CAD-CAM methods. Finally, the secondary/tertiary constructions can be generated and machined by software.

The essential point for the last aspect of the present invention is the use of a primary part as an adapter in order to be able to provide a shared placement direction for a denture part that pertains to several tooth stumps, implantation abutments and so on. Therewith, the use of more comprehensive denture parts is possible, parts which could not be employed without the present aspect of the invention, because so far it has not been possible for them to be placed on the substructure in the mouth due to the plurality of different placement directions that were necessary until now.

In particular, the embodiments above refer to the configurations specified in the claims and represent the concrete device and method characteristics of the claimed configurations, so that the relation of the terminologies in the embodiments and in the claims is immediately comprehensible and it is additionally clear that the embodiments and their characteristics and combinations of characteristics stand as examples for the statements in the claims and do not restrict the latter, but merely illustrate them.

The invention has been presented on the basis of the embodiments in the description and the drawings merely for the sake of example and is not limited thereto, but rather comprises all variants, modifications, substitutions and combinations which the person skilled in the art can deduce from the present documents, particularly within the scope of the claims and the general representations in the introduction to this description, as well as from the description of the embodiments and depictions thereof in the drawing, and can combine with his expert knowledge as well as with prior art, particularly including the complete disclosures of the older applications cited in this description. In particular, all the individual characteristics and configuration possibilities of the invention and of its embodiments can be combined.

What is claimed is:

1. Surface mapping and/or generation device, with a device for mapping 3D data of at least one denture base object such as a tooth stump or an implantation abutment, and an environment thereof, as well as with a device for the data-based generation and production of a denture part incorporating the 3D data of the denture base object, wherein there are additionally provided: a device for determining and/or defining a placement direction of the denture part that is to be slipped onto the denture base object, as well as a device for determining and producing a primary part that is to be slipped onto the denture base object before the denture part and that yields a desired placement direction for the denture part which is different from the placement direction that exists for slipping the primary part onto the denture base object; and in that the device for data-based generation and production of a denture part is designed to generate and produce the latter by incorporating the 3D data of the primary part.

2. Surface mapping and/or generation device according to claim 1, wherein a combination device is further provided designed for the assembly of 3D data from at least two denture base objects in shape, position and attitude to one another, and in that the device for producing a denture part is designed to produce one shared denture part for all the denture base objects involved.

3. Surface mapping and/or generation device according to claim 1, wherein a non-contact mapping device is included for mapping shape, position and/or attitude of each denture base object and/or of each primary part.

4. Surface mapping and/or generation devices according to claim 1, wherein, for determining and/or defining and/or generating and/or producing measurement data, 3D data and data records, archive and/or specification data and/or data records as well as placement directions, an electronic processing device is provided that contains a processor, storage, interfaces and controls.

5. Surface mapping and/or generation device according to claim 1, wherein a CAD-CAM device is included.

6. Surface mapping and/or generation device according to claim 1, wherein a remote data transmission device is included for spatially separating from one another the mapping device and the generation device and/or production device.

7. Surface mapping and/or generation device according to claim 6, wherein a plurality of mapping devices set up spatially separated from one another are coupled to one central generation device.

8. Surface mapping and/or generation method, wherein 3D data from a denture base object such as a tooth stump or an implantation abutment and an environment thereof are acquired and then, based on these 3D data of the denture base object, a denture part to be slipped thereon is produced, wherein: before production of the denture part, a placement direction of the denture part onto the denture base object is determined and/or defined; on the basis of this 3D data of the denture base object, a primary part is determined and produced, with which a desired placement direction that differs from the placement direction that exists for slipping the primary part onto the denture base object is created for the denture part; and, on the basis of the 3D data, the denture part is generated and produced based on data so as to fit when pushed upon the primary part.

9. Surface mapping and/or generation method according to claim 8, wherein 3D data from at least two denture base objects are acquired regarding their shape, position and attitude to one another, and in that a single denture part for all the denture base objects involved is produced and generated on the basis of data.

10. Surface mapping and/or generation method according to claim 9, wherein 3D data from at least 2 denture base objects are acquired regarding their shape, position and attitude to one another and then are assembled.

11. Surface mapping and/or generation method according to claim 8, wherein the mapping of shape, position and/or attitude of each denture base object and/or each primary part is done without contact.

12. Surface mapping and/or generation method according to claim 8, wherein measurement data, 3D data and data records, archive and/or specification data and/or data records, as well as placement directions from a measuring device and/or memory device are employed.

13. Surface mapping and/or generation method according to claim 12, wherein data of prefabricated parts from databases are employed.

14. Surface mapping and/or generation method according to claim 8, wherein a CAD-CAM device is used.

15. Surface mapping and/or generation method according to claim 8, wherein the mapping of an object and the acquisition of its 3D data and data records is accomplished spatially separated from the production of primary parts and/or denture parts by way of remote data transmission.

16. Surface mapping and/or generation method according to claim 15, wherein a mapping at a plurality of locations is coupled by remote data transmission to central mapping and/or production.

17. Surface mapping and/or generation device, according to claim 1, wherein a device is included for edge recognition of inlay preparations.

18. Surface mapping and/or generation device, according to claim 1, wherein a device for producing a complex denture design is included.

19. Surface mapping and/or generation method, according to claim 8, including a method step for edge recognition of inlay preparations.

20. Surface mapping and/or generation method, according to claim 8, including a method step for producing a complex denture design.

* * * * *

UNITED STATES PATENT AND TRADEMARK OFFICE
CERTIFICATE OF CORRECTION

| | | |
|---|---|---|
| PATENT NO. | : 7,899,221 B2 | |
| APPLICATION NO. | : 11/095027 | |
| DATED | : March 1, 2011 | |
| INVENTOR(S) | : Gerhard Weber et al. | |

It is certified that error appears in the above-identified patent and that said Letters Patent is hereby corrected as shown below:

In column 13, line 15:    please amend "pots by 450" to read "pots by 45°"

Signed and Sealed this
Fourteenth Day of June, 2011

David J. Kappos
*Director of the United States Patent and Trademark Office*